United States Patent
Caruso et al.

(10) Patent No.: US 9,283,216 B2
(45) Date of Patent: *Mar. 15, 2016

(54) ABUSE-RESISTANT CONTROLLED-RELEASE OPIOID DOSAGE FORM

(71) Applicant: Purdue Pharma L.P., Stamford, CT (US)

(72) Inventors: Frank S. Caruso, Colts Neck, NJ (US); Huai-Hung Kao, Syosset, NY (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/859,195

(22) Filed: Sep. 18, 2015

(65) Prior Publication Data

US 2016/0008346 A1    Jan. 14, 2016

Related U.S. Application Data

(60) Continuation of application No. 14/725,369, filed on May 29, 2015, now Pat. No. 9,161,937, which is a continuation of application No. 14/067,821, filed on Oct. 30, 2013, now Pat. No. 9,084,729, which is a continuation of application No. 13/777,537, filed on Feb. 26, 2013, now abandoned, which is a continuation of application No. 13/494,431, filed on Jun. 12, 2012, now abandoned, which is a continuation of application No. 11/901,232, filed on Sep. 14, 2007, now abandoned, which is a division of application No. 10/143,111, filed on May 10, 2002, now abandoned.

(60) Provisional application No. 60/290,439, filed on May 11, 2001.

(51) Int. Cl.
| A61K 31/485 | (2006.01) |
| A61K 9/20   | (2006.01) |
| A61K 9/00   | (2006.01) |
| A61K 31/46  | (2006.01) |

(52) U.S. Cl.
CPC .. *A61K 31/46* (2013.01); *A61K 9/20* (2013.01)

(58) Field of Classification Search
CPC . A61K 9/2018; A61K 9/2027; A61K 9/2054; A61K 9/20; A61K 9/0002; A61K 31/485; A61K 2300/00; A61K 8/25; A61K 8/26; A61K 8/042; A61K 8/0216; A61K 8/062; A61K 2800/10; A61K 2800/20; A61Q 19/00; A61Q 1/02; A61Q 19/08; A45D 40/262
See application file for complete search history.

(56) References Cited

U.S. PATENT DOCUMENTS

| 2,770,569 A | 11/1956 | Fromherz et al. |
| 3,133,132 A | 5/1964 | Loeb et al. |
| 3,173,876 A | 3/1965 | Zobrist |
| 3,173,877 A | 3/1965 | Jackson et al. |
| 3,276,586 A | 10/1966 | Rosaen |
| 3,332,950 A | 7/1967 | Blumberg et al. |
| 3,493,657 A | 2/1970 | Lewenstein et al. |
| 3,541,005 A | 11/1970 | Strathmann et al. |
| 3,541,006 A | 11/1970 | Bixler et al. |
| 3,546,876 A | 12/1970 | Fokker et al. |
| 3,676,557 A | 7/1972 | Lachman et al. |
| 3,773,955 A | 11/1973 | Pachter et al. |
| 3,845,770 A | 11/1974 | Theeuwes et al. |
| 3,879,555 A | 4/1975 | Pachter et al. |
| 3,916,889 A | 11/1975 | Russell |
| 3,916,899 A | 11/1975 | Theeuwes et al. |
| 3,950,508 A | 4/1976 | Mony et al. |
| 3,965,256 A | 6/1976 | Leslie |
| 3,966,940 A | 6/1976 | Patcher |
| 4,063,064 A | 12/1977 | Saunders et al. |
| 4,088,864 A | 5/1978 | Theeuwes et al. |
| 4,126,684 A | 11/1978 | Robson et al. |
| 4,160,020 A | 7/1979 | Ayer et al. |
| 4,176,186 A | 11/1979 | Goldberg |
| 4,200,098 A | 4/1980 | Ayer et al. |
| 4,216,314 A | 8/1980 | Raabe et al. |
| 4,237,140 A | 12/1980 | Dudzinski |
| 4,285,987 A | 8/1981 | Ayer et al. |

(Continued)

FOREIGN PATENT DOCUMENTS

| AU | 2002305559 | 11/2002 |
| CA | 2382648 | 3/2001 |

(Continued)

OTHER PUBLICATIONS

Abdulla et al., "Axotomy reduces the effect of analgesic opioids yet increases the effect of nociceptin on dorsal root ganglion neurons"; J of Neuro Sci (1998) vol. 18, pp. 9685-9694.

(Continued)

*Primary Examiner* — Blessing M Fubara
(74) *Attorney, Agent, or Firm* — Dechert LLP

(57) ABSTRACT

Abuse-resistant, controlled release opioid tablets are a combination containing an opioid antagonist such as naloxone at a level above that needed to suppress the euphoric effect of the opioid, if the combination were crushed to break the controlled release properties causing the opioid and opioid antagonist to be released as a immediate release product as a single dose. The controlled release nature of the table prevents the accumulation of orally effective amounts of opioid antagonist when taken normally. The opioid antagonist is contained in a controlled-release matrix and released, over time, with the opioid.

30 Claims, No Drawings

(56) References Cited

U.S. PATENT DOCUMENTS

| | | |
|---|---|---|
| 4,293,539 A | 10/1981 | Ludwig et al. |
| 4,366,310 A | 12/1982 | Leslie |
| 4,401,672 A | 8/1983 | Portoghese et al. |
| 4,443,428 A | 4/1984 | Oshlack et al. |
| 4,451,470 A | 5/1984 | Ganti |
| 4,457,933 A | 7/1984 | Gordon |
| 4,464,378 A | 8/1984 | Hussain et al. |
| 4,573,995 A | 3/1986 | Chen et al. |
| 4,582,835 A | 4/1986 | Lewis et al. |
| 4,608,376 A | 8/1986 | Pasternak |
| 4,661,492 A | 4/1987 | Lewis et al. |
| 4,668,685 A | 5/1987 | Shami |
| 4,719,215 A | 1/1988 | Goldberg |
| 4,722,928 A | 2/1988 | Boswell et al. |
| 4,730,048 A | 3/1988 | Portoghese et al. |
| 4,760,069 A | 7/1988 | Rzeszotarski et al. |
| 4,769,372 A | 9/1988 | Kreek |
| 4,785,000 A | 11/1988 | Kreek et al. |
| 4,803,208 A | 2/1989 | Pasternak |
| 4,806,341 A | 2/1989 | Chien et al. |
| 4,806,543 A | 2/1989 | Choi |
| 4,806,558 A | 2/1989 | Wuest et al. |
| 4,828,836 A | 5/1989 | Elger et al. |
| 4,834,965 A | 5/1989 | Martani et al. |
| 4,834,984 A | 5/1989 | Goldie et al. |
| 4,834,985 A | 5/1989 | Elger et al. |
| 4,844,907 A | 7/1989 | Elger et al. |
| 4,844,909 A | 7/1989 | Goldie et al. |
| 4,844,910 A | 7/1989 | Leslie et al. |
| 4,861,598 A | 8/1989 | Oshlack |
| 4,861,781 A | 8/1989 | Goldberg |
| 4,867,985 A | 9/1989 | Heafield et al. |
| 4,873,076 A | 10/1989 | Fishman et al. |
| 4,882,335 A | 11/1989 | Sinclair |
| 4,889,860 A | 12/1989 | Rzeszotarski et al. |
| 4,935,428 A | 6/1990 | Lewis |
| 4,940,587 A | 7/1990 | Jenkins et al. |
| 4,957,681 A | 9/1990 | Klimesch et al. |
| 4,970,075 A | 11/1990 | Oshlak |
| 4,987,136 A | 1/1991 | Kreek et al. |
| 4,990,341 A | 2/1991 | Goldie et al. |
| 5,071,646 A | 12/1991 | Malkowska et al. |
| 5,075,341 A | 12/1991 | Mendelson et al. |
| 5,086,058 A | 2/1992 | Sinclair et al. |
| 5,091,189 A | 2/1992 | Heafield et al. |
| 5,096,715 A | 3/1992 | Sinclair |
| 5,102,887 A | 4/1992 | Goldberg |
| 5,130,311 A | 7/1992 | Guillaumet et al. |
| 5,149,538 A | 9/1992 | Granger et al. |
| 5,215,758 A | 6/1993 | Krishnamurthy |
| 5,225,440 A | 7/1993 | London et al. |
| 5,236,714 A | 8/1993 | Lee et al. |
| 5,256,669 A | 10/1993 | Askanazi et al. |
| 5,266,331 A | 11/1993 | Oshlack at al. |
| 5,273,760 A | 12/1993 | Oshlack et al. |
| 5,286,493 A | 2/1994 | Oshlack et al. |
| 5,316,759 A | 5/1994 | Rose et al. |
| 5,317,022 A | 5/1994 | Borsodi et al. |
| 5,321,012 A | 6/1994 | Mayer et al. |
| 5,324,351 A | 6/1994 | Oshlack et al. |
| 5,336,691 A | 8/1994 | Raffa et al. |
| 5,352,680 A | 10/1994 | Portoghese et al. |
| 5,352,683 A | 10/1994 | Mayer et al. |
| 5,356,467 A | 10/1994 | Oshlack et al. |
| 5,356,900 A | 10/1994 | Bihari et al. |
| 5,376,662 A | 12/1994 | Ockert |
| 5,409,944 A | 4/1995 | Black et al. |
| 5,411,745 A | 5/1995 | Oshlack et al. |
| 5,426,112 A | 6/1995 | Zagon et al. |
| 5,436,265 A | 7/1995 | Black et al. |
| 5,457,208 A | 10/1995 | Portoghese et al. |
| 5,460,826 A | 10/1995 | Merrill et al. |
| 5,472,712 A | 12/1995 | Oshlack et al. |
| 5,472,943 A | 12/1995 | Crain |
| 5,474,995 A | 12/1995 | Ducharme et al. |
| 5,478,577 A | 12/1995 | Sackler et al. |
| 5,486,362 A | 1/1996 | Kitchell et al. |
| 5,500,227 A | 3/1996 | Oshlack et al. |
| 5,502,058 A | 3/1996 | Mayer et al. |
| 5,508,042 A | 4/1996 | Oshlack et al. |
| 5,508,043 A | 4/1996 | Krishnamurthy |
| 5,510,368 A | 4/1996 | Lau et al. |
| 5,512,578 A | 4/1996 | Crain |
| 5,514,680 A | 5/1996 | Weber et al. |
| 5,521,213 A | 5/1996 | Prasit et al. |
| 5,534,492 A | 7/1996 | Aston et al. |
| 5,536,752 A | 7/1996 | Ducharme et al. |
| 5,549,912 A | 8/1996 | Oshlack et al. |
| 5,550,142 A | 8/1996 | Ducharme et al. |
| 5,552,422 A | 9/1996 | Gauthier et al. |
| 5,556,838 A | 9/1996 | Mayer et al. |
| 5,574,052 A | 11/1996 | Rose et al. |
| 5,578,725 A | 11/1996 | Portoghese et al. |
| 5,580,578 A | 12/1996 | Oshlack et al. |
| 5,580,876 A | 12/1996 | Crain |
| 5,585,348 A | 12/1996 | Crain et al. |
| 5,591,452 A | 1/1997 | Miller et al. |
| 5,592,310 A | 1/1997 | Sugiura |
| 5,593,994 A | 1/1997 | Batt et al. |
| 5,601,845 A | 2/1997 | Buxton et al. |
| 5,604,253 A | 2/1997 | Lau et al. |
| 5,604,260 A | 2/1997 | Guay et al. |
| 5,616,601 A | 4/1997 | Khanna et al. |
| 5,622,722 A | 4/1997 | Knott et al. |
| 5,624,932 A | 4/1997 | Qin et al. |
| 5,633,259 A | 5/1997 | Qin et al. |
| 5,639,476 A | 6/1997 | Oshlack et al. |
| 5,639,780 A | 6/1997 | Lau et al. |
| 5,656,295 A | 8/1997 | Oshlack et al. |
| 5,670,172 A | 9/1997 | Buxton et al. |
| 5,672,360 A | 9/1997 | Sackler et al. |
| 5,681,585 A | 10/1997 | Oshlack et al. |
| 5,692,500 A | 12/1997 | Gaston-Johansson |
| 5,763,452 A | 6/1998 | Miller et al. |
| 5,767,125 A | 6/1998 | Crain |
| 5,780,479 A | 7/1998 | Kim |
| 5,811,126 A | 9/1998 | Krishnamurthy |
| 5,834,477 A | 11/1998 | Mioduszewski |
| 5,843,480 A | 12/1998 | Miller et al. |
| 5,849,240 A | 12/1998 | Miller et al. |
| 5,858,017 A | 1/1999 | Demopulos et al. |
| 5,860,950 A | 1/1999 | Demopulos et al. |
| 5,866,154 A | 2/1999 | Bahal et al. |
| 5,866,164 A | 2/1999 | Kuczynski et al. |
| 5,869,097 A | 2/1999 | Wong et al. |
| 5,879,705 A | 3/1999 | Heafield et al. |
| 5,880,132 A | 3/1999 | Hill |
| 5,891,471 A | 4/1999 | Miller et al. |
| 5,908,848 A | 6/1999 | Miller et al. |
| 5,942,241 A | 8/1999 | Chasin et al. |
| 5,958,452 A | 9/1999 | Oshlack at al. |
| 5,958,459 A | 9/1999 | Chasin et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 5,972,310 A | 10/1999 | Sachetto |
| 5,972,954 A | 10/1999 | Foss |
| 5,998,434 A | 12/1999 | Mitch et al. |
| 6,024,982 A | 2/2000 | Oshlack et al. |
| 6,068,855 A | 5/2000 | Leslie et al. |
| 6,077,532 A | 6/2000 | Malkowska et al. |
| 6,077,533 A | 6/2000 | Oshlack et al. |
| 6,096,756 A | 8/2000 | Crain et al. |
| 6,103,258 A | 8/2000 | Simon |
| 6,103,261 A | 8/2000 | Chasin et al. |
| 6,114,326 A | 9/2000 | Schueler |
| 6,143,322 A | 11/2000 | Sackler et al. |
| 6,143,328 A | 11/2000 | Heafield et al. |
| 6,159,501 A | 12/2000 | Skinhoj |
| 6,162,467 A | 12/2000 | Miller et al. |
| 6,194,382 B1 | 2/2001 | Crain et al. |
| 6,207,142 B1 | 3/2001 | Odds et al. |
| 6,210,714 B1 | 4/2001 | Oshlack et al. |

(56) References Cited

U.S. PATENT DOCUMENTS

| | | |
|---|---|---|
| 6,228,863 B1 | 5/2001 | Palermo |
| 6,254,887 B1 | 7/2001 | Miller et al. |
| 6,258,042 B1 | 7/2001 | Factor et al. |
| 6,261,599 B1 | 7/2001 | Oshlack et al. |
| 6,277,384 B1 | 8/2001 | Kaiko |
| 6,294,195 B1 | 9/2001 | Oshlack et al. |
| 6,306,438 B1 | 10/2001 | Oshlack et al. |
| 6,310,072 B1 | 10/2001 | Smith et al. |
| 6,326,027 B1 | 12/2001 | Miller et al. |
| 6,335,033 B2 | 1/2002 | Oshlack et al. |
| 6,362,194 B1 | 3/2002 | Crain et al. |
| 6,375,957 B1 | 4/2002 | Kaiko et al. |
| 6,387,404 B2 | 5/2002 | Oshlack |
| 6,395,705 B2 | 5/2002 | Crain et al. |
| 6,399,096 B1 | 6/2002 | Miller et al. |
| 6,419,959 B1 | 7/2002 | Walter at al. |
| 6,451,806 B2 | 9/2002 | Farrar |
| 6,475,494 B2 | 11/2002 | Kaiko et al. |
| 6,579,536 B1 | 6/2003 | Hirsch et al. |
| 6,596,900 B2 | 7/2003 | Blakemore et al. |
| 6,602,868 B2 | 8/2003 | McBrinn et al. |
| 6,627,635 B2 | 9/2003 | Palermo et al. |
| 6,696,066 B2 | 2/2004 | Kaiko et al. |
| 6,696,088 B2 | 2/2004 | Oshlack et al. |
| 6,706,281 B2 | 3/2004 | Oshlack et al. |
| 6,716,449 B2 | 4/2004 | Oshlack et al. |
| 6,743,442 B2 | 6/2004 | Oshlack et al. |
| 6,765,010 B2 | 7/2004 | Crain et al. |
| 7,172,767 B2 | 2/2007 | Kaiko et al. |
| 7,332,182 B2 | 2/2008 | Sackler |
| 7,419,686 B2 | 9/2008 | Kaiko et al. |
| 7,749,542 B2 | 7/2010 | Kaiko et al. |
| 8,105,631 B2 | 1/2012 | Kaiko et al. |
| 8,518,925 B2 * | 8/2013 | Fleischer ............ A61K 31/485 514/183 |
| 8,673,355 B2 | 3/2014 | Kaiko et al. |
| 8,822,487 B2 | 9/2014 | Kaiko et al. |
| 8,846,090 B2 * | 9/2014 | Brogmann ........... A61K 9/1617 424/464 |
| 8,846,091 B2 * | 9/2014 | Brogmann ........... A61K 9/1617 424/464 |
| 8,969,369 B2 * | 3/2015 | Caruso ................ A61K 9/2018 424/451 |
| 9,056,051 B2 * | 6/2015 | Caruso ................ A61K 9/2018 |
| 9,084,729 B2 * | 7/2015 | Caruso ................ A61K 9/2018 |
| 9,161,937 B2 * | 10/2015 | Caruso ................ A61K 9/2018 |
| 9,168,252 B2 * | 10/2015 | Caruso ................ A61K 31/485 |
| 2001/0006967 A1 | 7/2001 | Crain et al. |
| 2001/0018413 A1 | 8/2001 | Crain et al. |
| 2001/0053777 A1 | 12/2001 | Brecht |
| 2002/0006964 A1 | 1/2002 | Young et al. |
| 2002/0010127 A1 | 1/2002 | Oshlack et al. |
| 2002/0031552 A1 | 3/2002 | McTeigue et al. |
| 2002/0058673 A1 | 5/2002 | Kaiko et al. |
| 2003/0004177 A1 | 1/2003 | Kao |
| 2003/0044458 A1 | 3/2003 | Wright, IV et al. |
| 2003/0065002 A1 | 4/2003 | Caruso et al. |
| 2003/0069263 A1 | 4/2003 | Breder et al. |
| 2003/0073714 A1 | 4/2003 | Breder et al. |
| 2003/0092759 A1 | 5/2003 | Abuzzahab, Sr. |
| 2003/0118641 A1 | 6/2003 | Maloney et al. |
| 2003/0143269 A1 | 7/2003 | Oshlack |
| 2003/0178031 A1 | 9/2003 | DuPen et al. |
| 2003/0191147 A1 | 10/2003 | Sherman et al. |
| 2003/0229111 A1 | 12/2003 | Oshlack et al. |
| 2004/0052731 A1 | 3/2004 | Hirsh et al. |
| 2004/0092542 A1 | 5/2004 | Oshlack et al. |
| 2004/0176402 A1 | 9/2004 | Oshlack et al. |
| 2004/0186121 A1 | 9/2004 | Oshlack et al. |
| 2005/0063909 A1 | 3/2005 | Wright et al. |
| 2005/0095291 A1 | 5/2005 | Oshlack et al. |
| 2005/0163856 A1 | 7/2005 | Maloney et al. |
| 2005/0181046 A1 | 8/2005 | Oshlack et al. |
| 2005/0245483 A1 | 11/2005 | Brogmann et al. |
| 2005/0245556 A1 | 11/2005 | Brogmann et al. |
| 2005/0272776 A1 | 12/2005 | Buehler |
| 2006/0039970 A1 | 2/2006 | Oshlack et al. |
| 2006/0182801 A1 | 8/2006 | Breder et al. |
| 2007/0122348 A1 | 5/2007 | Kaiko et al. |
| 2007/0185146 A1 | 8/2007 | Fleischer et al. |
| 2008/0145429 A1 | 6/2008 | Leyendecker et al. |
| 2011/0172259 A1 | 7/2011 | Leyendecker et al. |
| 2012/0108621 A1 | 5/2012 | Brögmann et al. |
| 2012/0165359 A1 | 6/2012 | Kaiko et al. |
| 2012/0183612 A1 | 7/2012 | Brögmann et al. |
| 2012/0225901 A1 | 9/2012 | Leyendecker et al. |
| 2013/0165418 A1 | 6/2013 | Kaiko et al. |

FOREIGN PATENT DOCUMENTS

| | | |
|---|---|---|
| CA | 2478515 | 10/2003 |
| CA | 2478523 | 10/2003 |
| CA | 2372025 | 9/2007 |
| DE | 2138593 | 3/1972 |
| DE | 2222039 | 11/1972 |
| DE | 4325465 | 2/1995 |
| DE | 29719704 | 1/1998 |
| DE | 19651551 | 6/1998 |
| DE | 19857766 | 12/1999 |
| DE | 19859636 | 6/2000 |
| DE | 19918325 | 10/2000 |
| DE | 19938823 | 2/2001 |
| EP | 0193355 | 9/1986 |
| EP | 0205282 | 12/1986 |
| EP | 0319243 | 6/1989 |
| EP | 352361 | 1/1990 |
| EP | 527638 | 2/1993 |
| EP | 0576643 | 6/1993 |
| EP | 624366 | 11/1994 |
| EP | 631781 | 1/1995 |
| EP | 0647448 | 4/1995 |
| EP | 699436 | 3/1996 |
| EP | 0880352 | 2/1998 |
| EP | 0913152 | 5/1999 |
| EP | 1604666 | 12/2000 |
| EP | 1201233 | 5/2002 |
| EP | 1348429 | 10/2003 |
| EP | 1364649 | 11/2003 |
| EP | 1041987 B1 | 4/2006 |
| EP | 1695700 | 8/2006 |
| EP | 1813276 | 8/2007 |
| GB | 1353815 | 5/1974 |
| GB | 139072 A1 | 4/1975 |
| JP | H10-251149 | 9/1998 |
| NZ | 260408 | 5/1996 |
| NZ | 264953 | 11/1996 |
| NZ | 260883 | 6/1997 |
| NZ | 294897 | 10/1998 |
| NZ | 544181 | 12/2008 |
| RU | 98102450 | 7/1996 |
| RU | 2222260 | 1/2004 |
| WO | WO83/03197 | 9/1983 |
| WO | WO87/01282 | 3/1987 |
| WO | WO90/04965 | 5/1990 |
| WO | WO93/10765 | 6/1993 |
| WO | WO94/06426 | 3/1994 |
| WO | WO95/03804 | 2/1995 |
| WO | WO96/02251 | 2/1996 |
| WO | WO96/14058 | 5/1996 |
| WO | WO96/14059 | 5/1996 |
| WO | WO97/33566 | 9/1997 |
| WO | WO97/45091 | 12/1997 |
| WO | WO98/25613 | 6/1998 |
| WO | WO98/35679 | 8/1998 |
| WO | WO99/01111 | 1/1999 |
| WO | WO99/05960 | 2/1999 |
| WO | WO99/11250 A2 | 3/1999 |
| WO | WO99/22737 | 5/1999 |
| WO | WO99/32119 A1 | 7/1999 |
| WO | WO99/32120 A1 | 7/1999 |
| WO | WO00/01377 | 1/2000 |
| WO | WO00/25821 | 5/2000 |
| WO | WO00/38649 | 7/2000 |
| WO | WO00/41683 | 7/2000 |

(56) References Cited

FOREIGN PATENT DOCUMENTS

| | | |
|---|---|---|
| WO | WO00/51592 | 9/2000 |
| WO | WO00/67739 | 11/2000 |
| WO | WO01/32180 | 5/2001 |
| WO | WO01/37785 | 5/2001 |
| WO | WO01/52851 | 7/2001 |
| WO | WO01/58447 A1 | 8/2001 |
| WO | WO01/58451 A1 | 8/2001 |
| WO | WO01/68080 | 9/2001 |
| WO | WO01/85150 | 11/2001 |
| WO | WO01/85257 | 11/2001 |
| WO | WO01/93852 | 12/2001 |
| WO | WO02/087512 | 11/2002 |
| WO | WO02/092059 | 11/2002 |
| WO | WO02/092060 | 11/2002 |
| WO | WO03/003541 | 1/2003 |
| WO | WO03/004009 | 1/2003 |
| WO | WO03/007802 | 1/2003 |
| WO | WO03/013476 | 2/2003 |
| WO | WO03/013479 | 2/2003 |
| WO | WO03/013538 | 2/2003 |
| WO | WO03/020124 | 3/2003 |
| WO | WO03/024429 | 3/2003 |
| WO | WO03/024430 | 3/2003 |
| WO | WO03/026676 | 4/2003 |
| WO | WO03/070191 | 8/2003 |
| WO | WO03/073937 | 9/2003 |
| WO | WO03/084504 | 10/2003 |
| WO | WO-03084520 A2 | 10/2003 |
| WO | WO2004/026262 | 4/2004 |
| WO | WO2004/064807 | 8/2004 |
| WO | WO2004/091623 | 10/2004 |
| WO | WO2005/000310 | 1/2005 |
| WO | WO2005/025621 | 3/2005 |
| WO | WO2005/079760 | 9/2005 |
| WO | WO2005/120506 | 12/2005 |
| WO | WO2005/120507 | 12/2005 |
| WO | WO2006/024881 | 3/2006 |
| WO | WO2006/079550 | 8/2006 |
| WO | WO2006/089970 | 8/2006 |
| WO | WO2006/089973 | 8/2006 |
| WO | WO2007/047935 | 4/2007 |
| WO | WO2007/085637 | 8/2007 |
| WO | WO2007/088489 | 8/2007 |
| WO | WO2007/111945 | 10/2007 |
| WO | WO2007/123865 | 11/2007 |
| WO | WO2008/025790 | 3/2008 |
| WO | WO2008/030567 | 3/2008 |
| WO | WO2009/040394 | 4/2009 |
| WO | WO2010/003963 | 1/2010 |
| WO | WO2010/103039 | 9/2010 |
| WO | WO2012/020097 | 2/2012 |

OTHER PUBLICATIONS

Abernethy et al., "Randomised, double blind, placebo controlled crossover trial of sustained release morphine for the management of refractory dyspnoea," BMJ, vol. 327, pp. 1-6 (2003).
Alvarez-Fuentes et al. "Effectiveness of Repeated Administration of a New Oral Naltrexone Controlled-Release System in Morphine Analgesia"; J. Pharm Pharmacol (2001), 53:1201-1205.
Alvarez-Fuentes, et al., "Preclinical Study of an Oral Controlled Release Naltrexone Complex in Mice"; J. Pharm Pharmacol (2000), 52:659-663.
Amass et al., "Efficacy of daily and alternate-day dosing regimens with the combination buprenorphine-naloxone tablet"; Drug and Alcohol Dependence (2000) vol. 58, pp. 143-152.
Amati et al., "In vitro effects of naloxone on T-lymhpocyte-dependent antibacterial activity in hepatitis C virus (HCV) infected patients and in inflammatory bowel disease (IBD) patient," Immunopharmacology and Immonotoxicology, vol. 23, No. 1, pp. 1-11 (2001).
Archer Sydney; "Historical Perspective on the Chemistry and Development of Naltrexone"; Naltrexone Research Monograph28 (1980) p. 3-9.
Azamari et al., "Thermal treating as a tool for sustained release of indomethacin from Eudragit RS and RL matrices," International Journal of Pharmaceutics, 246, 171-177 (2002).
Barton et al., "Intranasal Administration of Naloxone by Paramedics";Prehospital Emergency Care (2002) vol. 6, No. 1, pp. 54-58.
Bashaw et al., "Relative bioavailability of controlled-release oral morphine sulfate during naltrexone blockade"; Inter J of Clin Pharm and Thea (1995) vol. 33, No. 9, 524-529.
Baum et al., "The Impact of the Addition of Naloxone on the Use and Abuse of Pentazocine"; Public Health Reports (1987) vol. 102, No. 4 p. 426-429.
Beauford et al., "Effects of Nebulized Morphine Sulfate on the Exercise Tolerance Ventilatory Limited COPD Patient," Chest, vol. 104, No. 1, pp. 175-178 (1993).
Benfey "Function of Myocardial-Adrenoceptors" ; Life Sciences (1982) vol. 31, pp. 101-112.
Benziger et al., "Differential effects of food on the bioavailability of cr oxycodone tablets and it oxycodone solution" J. Pharm. Sciences, vol. 85, No. 4, pp. 407-410 (1996).
Berkow, R. (ed.) Merck Manual of Medical Information, pp. 528-530 (1997).
Berkow, R. (ed.) The Merck Manual of Diagnosis and Therapy (1997), extract (English Translation from Russian).
Bigelow et al., "Abuse Liability and Assessment of Buprenorphine-Naloxone Combinations"; Dept of Psychiatry and Behavioral Sciences, The Johns Hopkins University School of Medicine, pp. 145-149, (1987).
Blachly Paul, H., M.D., "Naloxone in Opiate Addiction"; Current Psychiatric Therapies (1976) pp. 209-213.
Bloom et al., "Clinical Studies with Naloxone/Methadone in a Ratio of 1:20"; 5th National Conference on Methadone Treatment (1973) vol. 2, p. 1342-1349.
Brennscheidt et al., "Pharmacokinetics of Nortilidine and Naloxone after Administration of Tilidine/Naloxone Solution or Tilidine/Naloxone Sustained Release Tablets"; Arzeim-Forsch/Drug Res. (2000) vol. 50, pp. 1015-1022.
Briscoe et al., "Methoclocinnamox: Time Course of Changes in Alfetnanil-Reinforced Rhesus Monkeys"; Psychopharmacology (2000) 148:393-399.
Bromm et al., "A Sensitive Method to Evaluate Effects of Analgesics in Man"; Meth and Find Exptl Clin Pharmacol 5 (8) (1983) p. 545-551 (abstract).
Budd, Keith, "Clinical Use of Opioid Antagonists"; Bailliere's Clinical Anesthesiology (1987) vol. 1, No. 4, pp. 993-1011.
Bullingham et al., "Clinical Pharmacokinetics of Narcotic Agonist-Antagonist Drugs"; Clinical Pharm (1983) 8: 332-343.
Bunzow et al., "Molecular cloning and tissue distribution of a putative member of the rat opioid receptor gene family that is not a mu, delta or kappa opioid receptor type." FEBS Lett. Jun. 27, 1994;347(2-3):284-8.
Caldwell et al., "Treatment of Osteoarthritis Pain with Controlled Release Oxycodone or Fixed Combination Oxycodone Plus Acetaminophen Added to Nonsteroidal Antiinflammatory Drugs: A Double Blind, Randomized, Multicenter, Placebo Controlled Trial," J. Rheumatol. vol. 26, No. 4, pp. 862-869 (1999).
Calimlim, et al. "Effect of Naloxone on the Analgesic Activity of Methadone in a 1:10 Oral Combination"; Clin Pharmacol and There (1974) vol. 15; No. 6 pp. 556-564.
Cappel et al., "Enhancement of Naloxone Induced Analgesia by Pretreatment with Morphine" Pharma. Bioch. & Behav. (1989), 34:425-427.
Caruso et al., "Methadone and Naloxone in Combination (Naldone®) for the Treatment of Heroin Addicts"; Bristol Laboratories, pp. 1336-1341 (1973).
Chambers Dictionary of Science and Technology, Ed. P.M.B. Walker, Chambers, 1999, p. 803.
Chen et al., "Challenges and New Technologies of Oral Controlled Release," Oral Controlled Release Formulation Design and Drug Delivery: Theory to Practice (2010) pp. 257-277.
Chen et al., "Oral naloxone reverses opioid-associated constipation," Foreign Medical Sciences: Anesthesiology and Resuscitation, vol. 21, No. 5, p. 319 (2000).

(56) References Cited

OTHER PUBLICATIONS

Cherny Nathan I., "Opioid Analgesics"; Drugs May 1996:51 (5) pp. 713-737.
Cherry et al., "Opioids in pain therapy," The Frankfurt Consensus, STK—Special Issue 2001 Article 2 (3 pages) (in German, w/English translation).
Chiang et al. "Clinical Evaluation of a Naltrexone Sustained-Release Preparation"; Drug and Alcohol Dependence (1985) 16, pp. 1-8.
Chiang et al., "Kinetics of a Naltrexone Sustained-Release Preparation"; Clin Pharmacy Thera (1984) vol. 36 No. 5, pp. 704-708.
Chih-Cheng Chien et al., "Sigma Antagonists Potentiate Opioid Analgesia in Rats", Neuroscience Letters 190 (1995), 137-139.
Chinese Official Action dated Nov. 9, 2011 corresponding to Chinese Application No. 200680005969.1 relating to the instant application.
Choi et al., "Opioid Antagonists: A Review of Their Role in Palliative care, Focusing on Use in Opioid-Related Constipation," J. of Pain and Symptom Management, vol. 24(1): 71-90 (2002).
Ciccocioppo et al., "Effect of Nociceptin/orphanin FQ on the Rewarding Properties of Morphine"; Eur. J Pharmacol (2000) vol. 404, pp. 153-159.
Citron et al., "Long-term administration of controlled release oxycodone tablets for the treatment of cancer pain," Cancer Investigation, vol. 16, No. 8, pp. 562-571 (1998).
Clark et al., "Symptom indexes to assess outcomes of treatment for early prostate cancer" Medical Care 39(10): 1118-1130 (Oct. 2001).
Clemens et al., "Combined oral prolonged-release oxycodone and naloxone in opioid-induced bowel dysfunction: review of efficacy and safety data in the treatment of patients experiencing chronic pain," Expert Opinion on Pharmacotherapy, 11(2):297-310 (2010).
Cohen, "Statistical Power Analyses for the Behavioral Sciences" (2nd Ed.) Hilsdale, NJ: Erlbaum (1988).
Comer et al., "Depot Naltrexone: Long-lasting Antagonism of the Effects of Heroin un Humans"; Psychopharmacology (2002) 159, pp. 351-360.
Complaint for Declaratory Judgment filed in the United States District Court for the Western District Court of Virginia on Nov. 17, 2008, Civil Action No. 1:08CV00050.
Crabtree et al., "Review of Naltrexone, a long-acting Opiate Antagonist"; Clinical Pharmacy, vol. 3 (1984) pp. 273-280.
Crain et al., "Acute thermal hyperalgesia elicited by low-dose morphine in normal mice is blocked by ultra-low-dose naltrexone, unmasking potent opioid analgesia"; Brain Research (2001) vol. 888, pp. 75-82.
Crain et al., "Ultra-Low Concentrations of Naloxone Selectively Antagonize Excitory Effects of Morphine on Sensory Neurons, Thereby Increasing Its Antinociceptive Potency and Attenuating Tolerance/Dependence During Chronic Cotreatment," Proc. Natl. Acad. Sci. USA (1995) 92:10540-10544.
Crain, SM at al., "Antagonists of excitatory opioid receptor functions enhance morphine's analgesic potency and attenuate opioid tolerance/dependence liability" Pain, 84:121-131 (2000).
Culpepper-Morgan et al., "Treatment of opioid-induced constipation with oral naloxone: A pilot study." Clinical Trials and Therapeutics, (1992) vol. 52(1): 90-95.
Davies, S., "Rising to the pain challenge," Drug News Perspect, 19(10):653-8 (2006).
Delbarre et al., "Naloxone effects on blood pressure, analgesia and dieresis in spontaneous hypertensive and normotensice rats," Neuroscience Letters, vol. 30; pp. 167-172 (1982).
Deyo RA et al., "Reproducibility and responsiveness of health status measures. Statistics and strategies for evaltuttion." Cont. clin. Trials 12: 142S-158S (1991).
Di Giannuario et al., "Orphanin FQ reduces morphine-induced dopamine release in the nucleus accumbens: a microdialysis study in rats"; Neurosci. Lett (1999) vol. 272 pp. 183-186.
Dictionary of Modern Computer Terms, S.-P.: BHV-Petersburg, p. 215 (2004) (English translation).
Drossman DA et al., Rome II: The Functional Gastrointestinal Disorders (2nd ed.) McLean, VA: Dawson Associates (2000).

Ebell et al., eds. Die Schmerzebehandlung von Tumorpatienten, Thieme 1994 (Supportive Malinahmen in der Onkologie, Band 3) (in German, w/ Engl. Translation).
Eissenberg,E et al., "Buprenophine's physical dependence potential: Antagonist-precipitated withdrawal in humans" J. Pharmacol. Exp. Therapeut., 276(2):449 (1996).
Endo Opposition, filed by Mundipharma in AU against AU 2002305559, Oct. 1, 2008.
EP Application No. EP06111805.5: Jul. 10, 2008 Response to Office Communication dated Feb. 19, 2008.
EP Application No. EP10176720.0: Mar. 1, 2011 European Search Opinion and Search Report.
EP Application No. EP10180364.1: Office Communication and European Search Report, dated Dec. 12, 2010 (8 pages).
EP Application No. EP10180425.0: Office Communication and European Search Report, dated Dec. 12, 2010 (8 pages).
EP Application No. EP11177513.6: European Search Report and Search opinion dated Feb. 2, 2012.
EP Application No. EP11177516.9: European Search Report and Search opinion dated Feb. 2, 2012.
EP Application No. EP11177518.5: European Search Report and Search opinion dated Feb. 2, 2012.
EP Application No. EP11177520.1: European Search Report and Search opinion dated Feb. 2, 2012.
Excerpt from Industrial Pharmacy, "Classification of drug delivery systems," 1996 (English translation).
Extended European Search Report dated Apr. 12, 2012 corresponding to European Application No. 10176716.8.
Fink et al., "Naloxone in Heroin Dependence"; Clin Pharm and Thera. vol. 9, No. 5;pp. 568-577, (1968).
Fishman et al., "Disposition of Naloxone-7,8-3H in Normal & Narcotic Dependent Men"; J. Pharm. and Exper. Thera (1973)vol. 10 No. 2;pp. 575-580.
Forth et al., Allgemeine and Spezielle Pharmakologie un Toxikologie, 7. Auflage, 1996, Spektrum Akademischer Verlag, Heidelberg Berlin Oxford.
Foss et al., "Dose related Antagonism of the Emetic Effect of Morphine by Methylnaltrexone in Dogs",J. Clin Pharmacol (1993), 33:747-751.
Foss J.F., et al. Abstract, "Prevention of Apomorphine- or Cisplatin-induced emesis in the dog by combination of Methylnaltrexone and Morphine",Cancer Chemother Pharmacol (1998); 42(4):287-91.
Fraser Albert D., et al., "Clinical Toxicology of Drugs Used in the Treatment of Opiate Dependency"; Clinical Toxicology I (1990) vol. 10, No. 2; pp. 375-386.
Freye et al., 'Effects of Tramadol and Tilidine/Naloxone on Oral-Caecal Transit & Pupillary light Reflex'; Arzneim-Forsch/Drug Res. 50(I)(2000)pp. 24-30.
Fudala et al., "Effects of Buprenorphine and Naloxone in Morphine-Stabilized Opioid Addicts"; Drug and Alcohol Dependence 50 (1998) pp. 1-8.
Fudala et al., "Human Pharmacology and Abuse Potential of Nalmefene"; Clin Pharm and Thera (1991) vol. 49, 3, pp. 300-306.
Gal et al., "Prolonged Blockade of Opioid Effect with Oral Nalmefene"; Clin Pharm and Thera (1986) pp. 537-542.
Gan et al., "Opioid-Sparing Effects of a Low-Dose Infusion of Naloxone in Patient-Administered Morphine Sulfate," Anesthesiology (1997), 87(5):1075-1080.
Gerra et al., "Clonidine and Opiate Receptor Antagonists in the Treatment of Heroin Addiction"; J. Substance Abuse Treatment (1995) vol. 12, 1, pp. 35-41.
Ghodse et al., "Opioid analgesics and Narcotic Antagonists"; Side Effects of Drugs (2000) Annual 23, chpt 8 pp. 96-113.
Glatt William, M.D. FACP, "A New Method for Detoxifying Opioid-Dependent Patients"; J. Substance Abuse Treatment (1999) vol. 17, No. 3,pp. 193-197.
Gold et al. "Rapid Opioid Detoxification During General Anesthesia"; Anesthesiology (1999) vol. 91, No. 6, pp. 1639-1647.
Goliber (Benchtop Evaluations of Tampering with Pharmaceutical Dosage Forms, Opioid Abuse Resistance Conference, Oct. 2005—Accessed from http://www.thci.org/opioid/oct05docs/TAB%205.

(56) References Cited

OTHER PUBLICATIONS

8%20Gober.%20Benchtop%20Evaluations%20of%20Tampering%20with%20Pharmaceutical%20Disage%20Forms.pdf on Nov. 17, 2010.
Gonzalez et al., "Naltrexone: A Review of its Pharmacodynamic and Pharmacokinetic Properties and Therapeutic Efficacy in the Management of Opioid Dependence," Drugs (1988), 35:192-213.
Goodman and Gilman's The Pharmacological Basis of Therapeutics (Tenth Edition (2001), McGraw Hill.
Goodridge et al., "Factors associated with opioid dispensation for patients with COPD and lung cancer in the last year of life: A retrospective analysis," Int. J. of COPD, 2010, 5:99-105.
Greenwald et al., "Comparative Clinical Pharmacology of Short-Acting Opioids in Drug Abusers"; J. Pharm and Exper Thera (1996) vol. 277, No. 3, pp. 1228-1236.
Grimm, "Extension of the International Conference on Harmonization Tripartite Guideline for Stability Testing of New Drug Substances and Products to Countries of Climatic Zones III and IV," Drug Development and Industrial Pharmacy, vol. 24, No. 4, pp. 312-324 (1998).
Gupta et al., "Morphine Combined with Doxapram or Naloxone"; Anesthesia (1974) vol. 29, pp. 33-39.
Guyatt et al., "Interpreting treatment effects in randomized trials" Br. Med. J. 316(7132): 690-693 (1998).
Guyatt et al., "Measuring change over tune: assessing the usefulness of evaluative instruments" J. Chronic Dis. 40(2): 171-178 (1987).
Hagen, et al. "Efficacy, Safety, and Steady-State Pharmacokinetics of Once-A-Day Controlled-Release Morphine (MS Contin XL) in Cancer Pain," Journal of Pain and Symptom Management (2005) vol. 29, No. 1, pp. 80-90.
Han et al., "Muccoadhesive buccal disks for novel nalbuphine prodrug controlled delivery; effect of formulation variable on drug release and mucoadhesive performance"; International J. Pharm (1999) vol. 177, pp. 201-209.
Handal et al., "Naloxone"; Annals of Emergency Medicine (1983) vol. 12:7, pp. 438-445.
Hanson Analgesic, Antipyretic and Anti-Inflammatory Drugs in Remington's Science and Practice of Pharmacy (1995), 2:1207.
Harris et al., "Buprenorphine and Naloxone co-administration in opiate dependent patients stabilized on sublingual buprenorphine"; Drug and Alcohol Dependence (2000) vol. 61, pp. 85-94.
Hawkes et al., "Effect of enteric-release formulation of naloxone on intestinal transit in volunteers taking codeine"; Aliment Pharm Ther (2001) vol. 15, pp. 625-630.
Hays et al., "Assessing reliability and validity of measurement in clinical trials" in: Staquet at al., (eds.) Quality of Life in Clinical Trials: Methods and Practice Oxford: Oxford University Press (1998).
Hening et al., "Dyskinesias while awake and periodic movements in sleep in restless legs syndrome: Treatment with opioids," Neurology, vol. 36, pp. 1363-1366 (1986).
Hexal Opposition to related application EP 1492506, dated Sep. 30, 2009.
Hiroshi K., et al., "Pharmacology," Hirokawa Bookstore, 1992, p. 70-72.
Hogger et al., "Comparison of tilidine/naloxone, tramadol and bromfenac in experimental pain: a double-blind randomized crossover study in healthy human volunteers"; International J. Clin Pharm and Thera (1999) vol. 37, No. 8,pp. 377-385.
Holmes et al., "Inhibiting Spinal Dynorphin A Component Enhances Intrathecal Morphine Antinociception in Mice", Anesth. Analg. (1993), 77:1166-73.
Holzer et al., "Opioid-induced bowel dysfunction in cancer-related pain: causes, consequences and a novel approach for its management," Journal of Opioid Management, 5(3): 145-151 (2009).
Hopp et al., "Analgesic efficacy of oxycodone in combination with naloxone as prolonged release (PR) tablets in patients with moderate to severe chronic pain [abstract PT 226]," Presented at the 12th World Congress on Pain, International Association for the Study of Pain (IASP), Glasgow, Scotland, UK, MIS 4789879, Aug. 17-22, 2008.

Hopp et al., "Pain 2: Oral prolonged-release (PR) oxycodone/naloxone combination reduces opiod-induced bowel dysfunction (OIBD) in chronic pain patients [abstract 40]," Presented at the 5th Research Forum of the European Association for Palliative Care, Palliat. Med., 22(4):441 (2008).
Howes et al., "The Pharmacology of TR5109, a new Narcotic Agonist/Antagonist Analgesic"; NIDA Research (1979) pp. 99-105.
Hughes et al., "Buprenorphine for pain relief in a patient with drug abuse," The American Journal of Drug and Alcohol Abuse, vol. 17, No. 4, pp. 451-455 (1991).
Hussain et al., "Buccal and oral bioavailability of naloxone and naltrexone in rats";(1987) vol. 36, pp. 127-130.
Hussain, MA. "Improved buccal delivery of opioid analgesics and antagonists with bitterless prodrugs" Pharm. Res. 5(9): 615-618 (1988).
Inoue, "On the Treatment of Restless Legs Syndrome," Progress in RLS Research, vol. 24, No. 3, pp. 892-897 (2004).
Jasinski D.R., "Assessment of the Abuse Potentiality of Morphine-like Drugs (Methods Used in Man)"; Drug Addiction (1977) pp. 197-258.
Jasinski et al., "The human pharmacology and abuse potential of N-allylnoroxymorphone naloxone"; J. Pharm and Exper Thera (1967) vol. 157, No. 2, pp. 420-426.
Johnson et al., "Buprenorphine and Naloxone for Heroin Dependence"; Substance Use Disorders (2000) pp. 519-526.
Jones et al., "Nalmefene:blockade of intravenous morphine challenge effects in opioid abuse in humans"; Drug and Alcohol Dependence (2000) vol. 60, pp. 29-37.
Judson et al., "The Naloxone Test for Opiate Dependence," Clin. Pharmacol. Ther., vol. 27, No. 4, pp. 492-501, (1980).
Kanof et al., "Levels of Opioid Physical Dependence in Heroin Addicts," Drug and Alcohol Dependence, 27 (1991) 253-262.
Kanof, PD et al., "Clinical characteristics of naloxone-precipitated withdrawal in human opioid-dependent subjects" , Pharmacol. Exp. Therapeat, 260(1): 355 (1992).
Kapoor, S., "Emerging New Therapeutic Options for the Management of Opioid Induced Constipation," J. of Pain and Palliative Case Pharmacotherapy, 24(1):98-99 (2010).
Kazis et al., "Effects sizes for interpreting changes in health status", Med. Care 27(3 Suppl.): S178-S189 (1989).
King et al., "Naltrexone Biotransformation and Incidence of Subjective Side Effects: A Preliminary Study"; Alcoholism: Clin and Exper Res (1997) vol. 21, No. 5, pp. 906-909.
Kogan et al., "Estimation of the Systemic Availability and Other Pharmacokinetic Parameters of Naltrexone in Man after Acute and Chronic Oral Administration"; Res. Comm. in Chem. Path. and Pharm (1977) vol. 18, No. 1, pp. 29-34.
Kosten et al., "Opioid antagonist challenges in buprenorphine maintained patients"; Drug and Alcohol Dependence (1990) vol. 25, OO. 73-78.
Kosten Thomas R., M.D.,"Buprenorphine for Benzodiazepine-Abusing Heroin Addicts"; Amer J of Psychiatry (1994) vol. 1, p. 151.
Kreek et al., "Drug Interactions with Methadone," *Ann. N.Y. Acad. Sci.*, 281, 350-371 (1976).
Krylov, Drug Register of Russia, Encyclopedia of Drugs, (2001) entries for "Nalbuphine," "Naloxone," and "Naltrexone" (English Translation).
Kurland et al., "Naloxone and the Narcotic Abuser: A Cont oiled Study of Partial Blockade"; Inter. J. of the Addictions (1974) vol. 9, No. 5, pp. 663-672.
Kurz et al., "Opioid-Induced Bowel Dysfunction: Pathophysiology and Potential New Therapies," Drugs, vol. 63, No. 7, pp. 649-671 (2003), Abstract.
Lapierre "Acetaminophen Boosts Liver Toxicity Alone, as Combination Therapy—Jama" Health News Daily, vol. 18 Issue 128 dated Jul. 6, 2006.
Latasch et al., "Aufhebun einer Morphin-induzierten Obstipation durch orales Naloxon," with translation ("Oral Naloxone Antagonizes Morphine-Induced Constipation"), *Anaesthesist*, 46, 191-194 (1997).
Lee et al., "Nalbuphine Coadministered with Morphine Prevents Tolerance and Dependence"; Anesth Analg (1997) vol. 84, pp. 810-815.

(56) References Cited

OTHER PUBLICATIONS

Leehey et al., "Naloxone increases water and electrolyte excretion after water loading in patients with cirrhosis and ascites," J. Lab. Clin. Med., vol. 118, No. 5, pp. 484-491 (1991).

Leeling et al., "Disposition and metabolism of codorphone in the rat, dog, and man"; Drug Metabolism and Disposition (1982) vol. 10, No. 6, pp. 649-653.

Lehman et al.,"Influence of Naloxone on the Postoperative Analgesic and Respiratory effects of Buprenorphine"; Eur. J. Clin Pharm (1988) vol. 34, pp. 343-352.

Leidy et al., "Recommendations for evaluating the validity of quality of life claims for labeling and promotion" Value in Health 2(2): 113-127 (1999).

Levine et al., "Potentiation of Pentazocine Analgesia by Low-dose Naloxone"; J Clin Invest (1988) vol. 82, pp. 1574-1577.

Levy M.H., "Advancement of opioid analgesia with controlled-release oxycodone," Eur. J. Pain, vol. 5, Suppl. A, pp. 113-116 (2001), Abstract.

Li Chen et al., "Oral naloxone reverses opioid-associated constipation" Foreign Medical Sciences: Anaesthesiology and Resuscitation, 21(5):319 (2000).

Light et al., "Effects of Oral Morphine in Breathlessness and Exercise tolerance in Patients with Chronic Obstructive Pulmonary Disease," Am. Rev. Respir. Dis., (1989) vol. 139, pp. 126-133.

Liu et al., "Low dose oral naloxone reverses opioid-induced constipation and analgesia," Journal of Pain and Symptom Management, vol. 23, No. 1, pp. 48-53 (2002).

Loimer et al., "Combined Naloxone/Methadone Preparations for Opiate Substitution Therapy"; J. of Substance Abuse Treatment (1991) vol. 8, pp. 157-160.

Lorcet, Physicians' Desk Reference 48th ed., 1994; pp. 2388-2390.

Lortab, Physicians' Desk Reference 48th ed., 1994; pp. 2498-2500.

Lowenstein et al., "Combined prolonged release oxycodone and naloxone improves bowel function in patients receiving opioids for moderate-to-severe non-malignant chronic pain: a randomized controlled trial," Expert Opinion on Pharmacotherapy, 10(4):531-543 (2009).

*Markman* Opinion and Order (D.I. 156) in *King Pharm., Inc.* et al. v. *Purdue Pharma L.P.*, No. 1:08-cv-00050 (W.D. Va. Jun. 22, 2010).

Martin et al. "Bioavailability Investigation of a New Tilidine/Naloxone Liquid Formulation Compared to a Reference Formulation";Arzneim-Forsch./Drug Res. (1999) vol. 49, pp. 599-607.

Martin et al., "Demonstration of Tolerance to and Physical Dependence on N-allynormorphine (Nalorphine)";J. of Pharm and Exper Thera (1965) vol. 150, No. 3. pp. 437-442.

Medzon, R, "Naltrexone and Nalmefene," Clinical Toxicology Review, vol. 19, No. 3, Dec. 1996.

Meissner et al., "Oral naloxone reverses opioid-associated constipation", Pain, vol. 84, pp. 105-109 (2000).

Meissner, W et al., "A randomised controlled trial with prolonged-release oral oxycodone and naloxone to prevent and reverse opioid-induced constipation", Eur. J. Pain, 13: 56-64 (2009).

Mendelson et al., "Buprenophine and naloxone Interactions in Methadone Maintenance Patients"; Society of Biological Psychiatry (1997) vol. 41, pp. 1095-1101.

Mendelson et al., "Buprenorphine and naloxone combinations: the effects of three dose ratios in morphine stabilized, opiate-dependent volunteers"; Psychopharmacology (1999) vol. 141, pp. 37-46.

Mendelson J., et al, "Buprenorphine and Naloxone Interactions in Opiate Dependent Volunteers," Clin. Phar. Ther. (1996), 60:105-114.

Miaskowski et al., "Inhibition of Spinal Opioid Analgesia by Supraspinal Administration of Selective Opioid Antagonists", Brain Research (1992), 596:41-45).

Mikus, G., "Combining Opioid Agonists and Antagonists as a Solution for Opioid-induced Constipation," European Gastroenterology and Hepatology Review, 4(2):71-74 (2008).

Mims, Jan. 2005, pp. 120-125.

Mollereau et al., "ORL 1, a novel member of the opioid receptor family: Cloning, functional expression and localization"; FEBS letters 341 (1994), pp. 33-38.

Mueller-Lissner, "Fixed Combination of Oxycodone with Naloxone: a New Way to Prevent and Treat Opioid-Induced Constipation." Adv. Ther. (2010) 27(9):581-590.

Muller-Lissner et al., "Oral Prolonged release (PR) oxycodone/naloxone combination reduced opioid-induced bowel dysfunction (OIBD) in patients with severe chronic pain (abstract 189)," Presented at the 2nd International Congress on Neuropathic Pain, Berlin, Germany, Published in Eur. J. Pain, 11(S1):582, Jun. 7-10, 2007.

Mundipharma Clinical Study Report A2-3759 "Validation of Bowel Function Index" dated Jun. 15, 2005 (Rev. Jul. 12, 2005).

Mundipharma Clinical Study Report OXN 2401 "Optimization of Naloxone-Oxycodone Ratio in Pain Patients" Final Version dated Jun. 3, 2005.

Nadstawek et al., "Patient assessment of the efficacy and tolerability of coadministered prolonged release oral oxycodone and naloxone in severe chronic pain (abstract SAT0375)," Presented at the 8th Annual European League Against Rheumatism (EULAR 2007), Barcelona, Spain, Published in Ann. Rheum. Dis., 66(Suppl. 2):543, Jun. 13-16, 2007.

Nadstawek, J at al., "Patient assessment of a novel therapeutic approach for the treatment of severe chronic pain" Int. J. Clin. Pract., 62(8): 1159-1167 (2008).

Neunschwander et al., Palliative Medicine at a Glance, 1999 (whole book).

Nichols et al., "Improved bowel function with a combination of oxycodone and naloxone (OXN) as prolonged-release (PR) tablets in patients with moderate to severe chronic pain (abstract PT225)," Presented at the 12th World Congress on Pain, International Association for the Study of Pain (IASP), Glasgow, Scotland, UK, Aug. 17-22, 2008.

Nolte, T., "Prolonged-release oxycodone/naloxone is effective and safe in cancer pain (abstract 66)," Encore presentation at the 12th World Congress on Pain, International Association for the Study of Pain (IASP), Glasgow, Scotland, UK, Aug. 17-22, 2008.

Nolte, T., "Prolonged-release oxycodone/naloxone is effective and safe in clinical use (abstract 275)," Encore presentation at the 5th Research Forum of the European Association for Palliative Care, Published in Palliative Medicine, 22(4):484-5 (2008).

Nolte, T., "Prolonged-release oxycodone/naloxone is effective and safe in clinical use (abstract PO325)," Presented at the 28th German Congress on Cancer, Published in Onkologie, Berlin, Germany, 31 (Suppl. 1):165-6, Feb. 20-23, 2008.

Norman et al., "Interpretation of changes in health-related quality of life. The remarkable universality of half a standard deviation" Med. Care, 41: 582-592 (2003).

Nunnally et al., Psychometric Theory, ($3^{rd}$ ed.) NY: McGraw-Hill (1994).

Nutt et al., "Methadone-naloxone mixture for use in methadone maintenance programs"; Clin Pharm and Ther. vol. 15, No. 2., pp. 156-166 (1974).

Oppermann M., "Neue Arzneimittel zur Behandlung der Opioid-induzierten Obstipation: der Mechanismus-basierte Ansatz von Methylnaltrexon, Naloxon and Alvimopan," Fortbildungstelegramm Pharmazie; 1 Mai; vol. 3, pp. 117-131 (2009).

Oxygesic® Product Information, 1997-2001 (in German, w/ English translation).

Package Insert for OxyContin®, Purdue Pharma L.P. (Mar. 18, 2004).

Paille et al., "An open six-month study of the safety of Transipeg for treating constipation in community medicine," J. Clin. Res., vol. 2, pp. 97-254 (1999).

Pamuk et al., "Revalidation of description of constipation in terms of recall bias and visual scale analog questionnaire," Journal of Gastroenterology and Hepatology (2003), 18, 1417-1422.

Pappagallo, M., "Incidence, prevalence, and management of opioid bowel dysfunction," Am. J. Surg. (2001) 182 suppl. 11S-18S.

Paronis et al., "Increased Analgesic Potency of Mu Agonists after Continuous Naloxone Infusion in Rats"; J for Pharm Exper Thera (1991), 259 (2), pp. 582-589.

(56) References Cited

OTHER PUBLICATIONS

Parwartikar et al., "Naloxone-Methadone Combination for the Treatment of Opiate Dependence"; Missouri Institute of Psychiatry, pp. 1350-1354, (1973).
Parwatikar et al., "Methadone-naloxone in combination for the Treatment of Heroin Addicts"; Clin. Pharm and Thera, vol. 14, No. 6, pp. 941-948,(1973).
PCT Application PCT/EP2003/003540: International Preliminary Examination Report dated Aug. 17, 2004.
PCT Application PCT/EP2005/006155: International Search Report and Written Opinion of the International Searching Authority dated Aug. 25, 2005.
PCT Application PCT/EP2005/006155: International Search Report dated Aug. 25, 2005 (2 pages).
PCT Application PCT/EP2006/060336: International Preliminary Report on Patentability and Written Opinion of the International Searching Authority dated May 18, 2007.
PCT Application PCT/EP2006/060341: International Preliminary Report on Patentability and Written Opinion of the International Searching Authority dated May 16, 2007.
PCT Application PCT/EP2008/062834: International Preliminary Report on Patentability and Written Opinion of the International Searching Authority dated Mar. 30, 2010.
PCT Application PCT/EP2009/058630: International Search Report and Written Opinion of the International Searching Authority dated Oct. 9, 2009.
Peachey et al., "Assessment of Opioid Dependence with Naloxone," British Journal of Addiction (1988) 83(2), 193-201.
Philippe et al., "Mu opoid receptor expression is increased in inflammatory bowel diseases: implications for homeostatic intestinal inflammation," GUT, vol. 55, No. 6, pp. 815-823 (2006).
Physician's Desk Reference (2001) see "Oxycontin," pp. 2697-2701.
Physician's Desk Reference (2001) see "Revia," pp. 1146-1149.
Physician's Desk Reference 48th ed.; 1994; "Talwin," 2120-2121, Montvale, NJ.
Pitts et al., "Antinociceptive and Response Rate-Altering Effects of Kappa Opioid Agonists, Spiradoline, Enadoline and U69,593, Alone and in Combination with Opioid Antagonists in Squirrel Monkeys"; J of Pharm and Ezper Thera (1994) vol. 271, No. 3, pp. 1501-1508.
Poole et al., "The Effect of Sustained-Release Morphine on Breathlessness and Quality of Life in Severe Chronic Obstructive Pulmonary Disease," Am. J. Respir. Crit. Care Med, vol. 157, pp. 1877-1880 (1998).
Portenoy et al., "Breakthrough pain: characteristics and impact in patients with cancer pain," Pain, vol. 81, pp. 129-134 (1999).
Portenoy et al., "Breakthrough pain: definition, prevalence and characteristics," Pain, vol. 41, pp. 273-281 (1990).
Press Release "International Patent Application to Be Published on Abuse-Resistant Pain Reliever Being Developed by Perdue Pharma"; Aug. 8, 2001.
Preston et al., "Abuse liability and studies of opioid agonist-antagonists in humans"; Drug and Alcohol Dependence (1991) vol. 28, pp. 49-82.
Preston et al., "Buprenorphine and Naloxone alone and in combination in Opioid-dependant Humans"; Psychopharmacology (1988), vol. 94, pp. 484-490.
Preston et al., "Differential Naltrexone Antagonism of Hydromorphone and Pentazocine Effects in Human Volunteers"; J of Pharm and Ezper Thera (1993) vol. 264, No. 2 pp. 813-823.
Preston et al., "Effects of Sublingually given naloxone in Opioid-dependant human volunteers"; Drug and Alcohol Dependence (1990) vol. 25, pp. 27-34.
Rapaka et al., "Discovery of Novel Opioid Medications"; NIDA Research Monograph 147 (1995) p. 55-83.
Rawal, et al., "An experimental study of urodynamic effects of epidural morphine and of naloxone reversal", Anesth Analg. Jul. 1983;62(7):641-647.
Reents et al., "Naloxone and Naltrexone Application in COPD," Chest, vol. 92, No. 1, pp. 217-219 (1988).

Reimer et al., "Meeting the challenges of opioid-induced constipation in chronic pain management—a novel approach," Pharmacology, 83:10-17 (2009).
Rentz et al., "Validation of the Bowel Function Index to detect clinically meaningful changes in opioid-induced constipation," Journal of Medical Economics (JME), 12(0):371-383 (2009).
Resnick et al., "Naloxone Precipitated Withdrawal: A Method for Rapid Induction Onto Naltrexone," Clinical Pharmacology and Therapeutics, vol. 21, No. 4, pp. 409-413; received for publication Nov. 16, 1976.
Revicki et al., "Recommendation on health-related quality of life research to support labeling and promotional claims in the United States", OOL Research 9(8): 887-900 (2000).
Richter et al., "Clinical Investigation on the Development of Dependence during Oral Therapy with Tramadol"; Arzniem-Forsch/Drug Res. 35 (No. II)(1985)pp. 1742-1744.
Rosen et al., "A Pilot Study of Dextromethorphan in Naloxone-Precipitated Opiate Withdrawal"; European J. of Pharm. (1996) vol. 307, pp. 251-257.
Rosen et al., "The effect of Lamotrigine on Naloxone-precipitated Opiate withdrawal"; Drug and Alcohol Dependence (1998) vol. 52, pp. 173-176.
Rosow et al., "Reversal of opioid-induced bladder dysfunction by intravenous naloxone and methylnaltrexone," Clin. Pharm. & Ther., vol. 82, No. 1, pp. 48-53 (2007).
Rote Liste 2004, Jan. 1, 2004; Frankfurt/Main, vol. 2004, pp. 05001-05033.
Sandner F., "Hope for patients with chronic pain: naloxone and oxycodone fixed combination offers analgesia and prevention of constipation also during sleep," J. of Pham. and Therapy, vol. 16; No. 6; pp. 179-180 (2007).
Sandner-Kiesling et al., "Long-term efficacy and safety of combined prolonged-release oxycodone and naloxone in the management of non-cancer chronic pain," International Journal of Clinical Practice, 64(6):763-774 (2010).
Schenck et al., "Letter to the Editor," Sleep Med., vol. 4, No. 3, p. 251 (2003).
Schenck et al., "Severe, childhood-onset, idiopathic, life-long insomnia responding selectively to opiate therapy: case report with 19 year follow-up," Sleep Med., vol. 2, No. 6, pp. 531-536 (2001).
Schmidt, W.K. "Alvimopan (ADL 8-2698) Is a Novel Peripheral Opioid Antagonist," The American Journal of Surgery, 182 (Suppl. to Nov. 2001) 27S-38S (2001).
Schuh et al., "Buprenorphine, Morphine and Naloxone Effects during Ascending Morphine Maintenance in Humans"; J. Pharm and Exper Thera (1996) vol. 278, 2, pp. 836-846.
Schuh et al., "Onset, Magnitude and Duration of Opioid Blockade Produced by Buprenorphine and Naltrexone in Humans"; Psychopharmacology (1999) vol. 145, pp. 162-174.
Schutter et al., "Innovative pain therapy with a fixed combination of prolonged-release oxycodone/naloxone: a large observational study under conditions of daily practice," Current Medical Research and Opinion, 26(6):1377-1387 (2010).
Shen et al., "Ultra-Low Doses of Naltrexone or Etorphine Increase Morphine's Antinocieceptive Potencey and Attenuate Tolerance/Dependence in Mice," Brain Research (1997), 757:176-190.
Shin Yakuzaigaku Soron (3rd revised edition), 1987, p. 148-151.
Simpson et al., "Fixed-ratio combination oxycodone/naloxone compared with oxycodone alone for the relief of opiod induced constipation in moderate-to-severe non-cancer pain," Current Medical Research and Opinion (CMRO), 24(12):3503-3512 (2008).
Smith et al., "Low-dose naltrexone as a treatment for active Crohn's disease," AGA Abstracts, S1397, XP009095749, p. A-218 (2006).
Smith et al., "Low-dose naltrexone therapy improves active Crohn's disease," The American Journal of Gastroenterology, vol. 102, No. 4 pp. 820-828 (2007).
Smith et al., "Single and multiple-dose pharmacokinetic evaluation of oxycodone and naloxone in an opioid agonist/antagonist prolonged-release combination in healthy adult volunteers," Clinical Therapeutics, 30(11):2051-2068(2008).
Smith et al., "Prolonged-release oxycodone/naloxone tablets: Dose-proportional pharmacokinetics (abstract PW 256)," Presented at the

(56) References Cited

OTHER PUBLICATIONS

12th World Congress on Pain, International Association for the Study of Pain (IASP), Glasgow, Scotland, UK (MIS 4790606), Aug. 17-22, 2008.
Stevens et al., Nonspecific Excitatory Effects of Morphine: Reverse-Order Precipitated Withdrawal and Dose-Dose Interactions': Psychopharmacology (1981) vol. 75, pp. 210-211.
Stine et al., "Reduction of Opiate Withdrawal-like Symptoms by Cocaine Abuse during Methadone and Buprenorphine Maintenance"; Am. J. Drug and Alcohol Abuse (1994) vol. 20, 4, pp. 445-458.
Stine et al., "Use of Drug Combinations in Treatment of Opioid Withdrawal"; J. Clinical Psych. (1992) vol. 12, No. 3, pp. 203-209.
Stoller et al., "Effects of buprenorphine/naloxone in opioid-dependent humans" Psychopharmacology (2001) vol. 154, pp. 230-242.
Strain et al., "Acute Effects of Buprenorphine, hydromorphone and naloxone in methadone-maintained volunteers"; J. Pharm and Exper Thera (1992) vol. 261, No. 3, pp. 985-993.
Strain et al., "Effects of buprenorphine versus buprenorphine/naloxone tablets in non-dependent opioid abusers"; Psychopharmacology (2000) vol. 148, pp. 374-383.
Strain et al., "Opioid antagonist effects of dezocine in opioid-dependent humans"; Clin Pharm and Thera (1996) vol. 60, No. 2, pp. 206-217.
Strain et al., "Precipitated Withdrawal by Pentazocine in Methadone-Maintained Volunteers"; J. Pharm and Exper Thera (1993) vol. 267, No. 2, pp. 624-634.
Sunshine et al., "Analgesic Efficacy of Pentazocine Versus a Pentazocine-Naloxone Combination Following Oral Administration," Clin. J. Pain (1988), 4:35-40.
Suzuki et al., "Morphine conditioned place preference after chronic treatment with naloxone in the rat"; Research Communications in Substance Abuse (1991) vol. 12., No. 3., pp. 119-131.
Sykes "An investigation of the ability of oral naloxone to correct opioid-related constipation in patients with advanced cancer," Palliative Medicine (1996), 10:134-144.
Sykes "Oral naloxone in opioid-associated constipation," Lancet (1991) vol. 337 p. 1475.
Sykes, N.P., "Using Oral Naloxone in Management of Opioid Bowel Dysfunction," in Handbook of Opioid Bowel Syndrome, Chapter 9, (Yuan, C.-S. ed., The Haworth Medical Press 2005).
Tai et al., "Naltrexone: An Antagonist Therapy for Heroin Addiction"; NIDA (1997) 5 pages.
Trzepacz et al., "Response to Opioids in Three Patients with Restless Legs Syndrome," Am. J. Psychiatry, vol. 141, pp. 993-999 (1984).
U.S. Appl. No. 13/329,218: Aug. 15, 2013 Reply to Non-Final Office Action dated Feb. 15, 2013 (application corresponds to US Publication Citation No. A36).
U.S. Appl. No. 13/329,218: Final Office Action dated Dec. 5, 2013.
U.S. Appl. No. 14/058,068: Nov. 22, 2013 Third Preliminary Amendment.
U.S. Appl. No. 14/058,068: Non-Final Office Action dated Dec. 16, 2013.
U.S. Appl. No. 60/290,439, filed May 11, 2001.
Umbricht et al., "Naltrexone shortened opioid detoxification with buprenorphine"; Drug and Alcohol Dependence (1999) vol. 56 pp. 181-190.
Vaccarino et al., "Endogenous Opiates: 1999"; Peptides 21 (2000) pp. 1975-2034.
Vaccarino et al., "Analgesia Produced by Normal Doses of Opioid Antagonists Alone and in Combination with Morphine", Pain (1989), 36:103-109.
Valaron® Product Information, 1997-2001 (in German, w/ English translation).
Vicodin, Physicians' Desk Reference 48th ed., 1994; pp. 1143-1145.
Vondrackova, D. et al., "Analgesic efficacy and safety of oxycodone in combination with naloxone as prolonged release tablets in patients with moderate to severe chronic pain", J. Pain 9(12):1144-1154 (Dec. 2008).

Walsh et al., "Effects of Naltrexone on Response to Intravenous Cocain, Hydromorphone and their Combination in Humans," (1996).
Walters et al., "Successful Treatment of the Idiopathic Restless Legs Syndrome in a Randomized Double-Blind Trial of Oxycodone Versus Placebo," Sleep, vol. 16, No. 4, pp. 327-332 (1993).
Wang et al., "cDNA cloning of an orphan opiate receptor gene family member and its splice variant"; FEBS letters 348 (1994) pp. 75-79.
Wang et al., "Crossover and Parallel Study of Oral Analgesics," J. Clin. Pharmacol (1981), 21:162-168.
Wang et al., "Inverse Agonists and neutral antagonists at mu opioid receptor (MOR): possible role of basal receptor signaling in narcotic dependence"; J. Neurochemistry (2001) vol. 77, pp. 1590-1600.
Wang et al., "Rating the Presence and Severity of Opiate Dependence," Clinical Pharmacology and Therapeutics, vol. 16, No. 4, pp. 653-657; received for publication Jan. 21, 1974.
Watkins et al "Aminotransferase Elevations in Healty Adults Receiving 4 Grams of Acetaminophen Daily" Jama, Jul. 5, 2006 vol. 296 No. 1.
Way et al., "Responsivity to Naloxone during Morphine Dependence"; Annals New York Academy of Sciences, pp. 252-261, (1976).
Weinberg et al., "Sublingual absorption of selected opioid analgesics"; Clin Pharm Thera (1988) vol. 44, No. 3, pp. 335-342.
Weinhold et al., "Buprenorphine Alone and in Combination with Naltrexone in Non-Dependent Humans," Drug and Alcohol Dependence (1992), 30:263-274.
Wells et al., "In vivo Pharmacological Characterization of SoRI 9409, a Nonpeptidic Opioid-Agonist/-Antagonist that Produces Limited Antinociceptive Tolerance and Attenuates Morphione Physical Dependence"; J. Pharm and Exper Thera (2001) vol. 297, No. 2, pp. 597-605.
Wiesen et al., "The Safety and Value of Naloxone as a Therapeutic Aid," Drug and Alcohol Dependence, 2 (1977) pp. 123-130.
Wikler et al., "N-Allylnormorphine: Effects of single dose and Precipitation of Acute "Abstinence Syndromes" during addiction to morphine, methadone or heroin in man (post addicts)"; J. Pharmacol. Exp. Ther., 109, 8-20 (1953).
Wilkinson, "The Dynamics of Drug Absorption, Distribution, and Elimination," Goodman and Gilman's The Pharmacological Basis of Therapeutics, Chapter 1, Pharmacokinetics, copyright page and pp. 3-29 (2001).
Wilmington, Del., PR Newswire; New Data Published Describing Favorable Safety Profile of REVIA (Naltrexone Hydrochloride Tablets) When Used to Treat Alcohol Dependence,' Dec. 1997.
Wodak Alex, "Drug Treatment for Opioid Dependence"; Australian Prescriber (2001) vol. 24, No. 1, pp. 4-6.
Woodward et al., "Prolonged-release oxycodone/naloxone tablets: Pharmacokinetics in the elderly (abstract)," Presented at the 12th World Congress on Pain, International Association for the Study of Pain (IASP), Glasgow, Scotland, UK, Abstract PW 255, (MIS 4789067), Aug. 17-22, 2008.
Wright et al., "Acute physical dependence in Humans; repeated naloxone-precipitated withdrawal after a single-dose of methadone"; Drug and Alcohol Dependence (1991) vol. 27, pp. 139-148.
Wyrwich et al,, "Further evidence supporting an SEM-based criterion for identifying meaningful intra-indivisual changes in health-related quality of life", J. Clin. Epidemiol., 52:861-873 (1991).
Yoburn et al., "Opioid Antagonist-induced Receptor Upregulation: Effects of Concurrent Agonist Administration"; Brain Research Bulletin (1994), vol. 33, pp. 237-240.
Yoburn et al., "Supersensitivity to Opioid Analgesics Following Chronic Opioid Antagonist Treatment: Relationship to Receptor Sensitivity"; Pharmacology Bio Beh (1995) vol. 51 No. 2, pp. 535-539.
Yuan et al., "Efficacy of Orally Administered Methylnaltrexone in Decreasing Subjective Effects After Intravenous Morphine", Drug and Alcohol Dependence (1998); 52:161-165.
Yuan et al., "The Safety and Efficacy of Oral Methylnaltrexone in Preventing Morphine-induced Delay in Oral-Cecal Transit Time", Clinical Trials and Therapeutics (1997), 61:467-475.
Zaks et al., "Naloxone Treatment of Opiate Dependence"; JAMA (1971) vol. 215, No. 13, pp. 2108-2110.

(56) References Cited

OTHER PUBLICATIONS

Zech et al., "Validation of World Health Organization Guidelines for Cancer Pain Relief: A 10-year prospective study" Pain 63: 65-76 (1995).

Zeppetella et al., "Opioids for cancer breakthrough pain: A pilot study reporting patient assessment of time to meaningful pain relief," J. of Pain and Symptom Management, vol. 25, No. 5, pp. 563-567 (2008).

Zhang et al., "Down-Regulation of -Opioid Receptors in Rat and Monkey Dorsal Root Ganglion Neurons and Spinal Cord After Peripheral Axotomy"; Neuroscience (1998) vol. 82., pp. 223-240.

Zou, W "A clinical analysis of 18 cases of naloxone treating pruritus due to cholestia, hebei", Modern Journal of Integrated Traditional Chinese and Western Medicaine 8(1):43 (1999).

Zhu et al., "Naltrexone-precipitated morphine withdrawal in infant rat is attenuated by acute administration if NOS inhibitors but not NMDA receptor antagonists"; Psychopharmacology (2000) vol. 150, pp. 325-336.

\* cited by examiner

ABUSE-RESISTANT CONTROLLED-RELEASE OPIOID DOSAGE FORM

CROSS REFERENCE TO RELATED APPLICATIONS

This application is a continuation of U.S. patent application Ser. No. 14/725,369, filed May 29, 2015, which is a continuation of U.S. patent application Ser. No. 14/067,821, filed Oct. 30, 2013 (now issued as U.S. Pat. No. 9,084,729), which is a continuation of U.S. patent application Ser. No. 13/777,537, filed Feb. 26, 2013, which is a continuation of U.S. patent application Ser. No. 13/494,431, filed Jun. 12, 2012, which is a continuation of U.S. patent application Ser. No. 11/901,232, filed Sep. 14, 2007, which is a divisional of U.S. patent application Ser. No. 10/143,111, filed May 10, 2002, which claims benefit of priority to U.S. Provisional Application No. 60/290,439, filed May 11, 2001.

FIELD OF THE INVENTION

The present invention relates to controlled-release analgesic pharmaceutical formulations. More specifically, the invention relates to abuse-deterring controlled-release analgesic tablets.

Opioid compounds have long been known both for their powerful analgesic properties, and for their strong potential for abuse. While highly effective at controlling pain, opioids can also be addictive. Abuse of opioids, particularly heroin, but also including morphine, codeine, oxycodone, hydromorphone, oxymorphone, and others, is a problem in modern society. Opioid addicts can obtain drugs from a variety of illicit sources. These street drugs are of questionable quality. Therefore, to potential abusers, prescription pharmaceutical opioids can be particularly attractive as a drug source because of their high purity and dependable dosage.

Abusers extract the pharmaceutical opioid, and other constituents, from the tablets. To do so, the tablets are crushed and often dissolved. The result may be further treated before it is ultimately injected or snorted to achieve a "high". This type of intravenous or intranasal abuse is well documented.

The potential for abuse of pharmaceutical opioids is not a new problem. To combat the effects of opioid abuse, opioid antagonists have been used to block the euphoria associated with opioid abuse, and to induce withdrawal symptoms in addicts. One opioid antagonist used previously, and even now, is naloxone. Naloxone is a powerful antagonist of the opioid receptor. Naloxone is highly effective when taken parenterally, but poorly effective when taken orally because of its metabolism in the liver and, thus, has a high oral:parenteral potency ratio. When injected in humans, amounts as small as 0.2-0.4 mg can block the opioid receptors and prevent the user from experiencing the drug's effects, whether analgesia or mood alteration, euphoria. Because of the high oral:parenteral potency ratio (~100) the antagonist action of oral doses of naloxone is much lower than the action of injections of naloxone. Because antagonists such as naloxone are less effective when taken orally, they have not been used to deter oral abuse and have been limited to deterring parenteral or intranasal abuse.

Recently however, a new form of abuse of opioid agonists has emerged involving oral abuse instead of abuse by injection or snorting. This practice has emerged largely because of the availability of high-opioid content controlled release (CR) formulations. "Chewing" involves crushing the opioid formulation and taking the entire contents, meant for 2 or more doses, at once. This practice releases all the opioid at once to generate a "high." The crushing may take place in the mouth as suggested by the name, but also may occur by other means to make the opioid readily available including, crushing or dissolving the tablet prior to injection or administered intranasally.

Recently, high potency prescription opioid tablets containing large milligram doses of opioids have been introduced. These tablets are controlled release tablets and are designed to provide pain relief for 12 hours or more. Because the tablets have action over a long time period (12 hours instead of 4 hours for immediate release tablets), the tablets contain much higher quantities of opioid compounds. For potential abusers, these tablets are very attractive. Their high dosages make them a compact way to access large amounts of opioid. The fact that they are pharmaceuticals guarantees both the quality and quantity of drug in the tablet. Thus, the potential abuser knows he or she is obtaining a high purity drug in a known dosage. Prior oral opioid dosage formulations contained relatively low doses of opioid and were not generally targets for oral abuse. Their immediate release formulations release the opioid all at once, but with low amounts of opioid that would not be sufficient for oral abuse without putting several low dosage units together. In contrast, abusers have found that the new CR tablets contain large doses of opioid, which can be abused orally by chewing the tablets or crushing them to release all of the opioid at one time (immediate release). The present invention deters such oral abuse.

Oxycontin®, a controlled release oxycodone tablet from Purdue Pharma, is available in strengths as high as 160 mg oxycodone per tablet. The high opioid content makes these tablets especially attractive to abusers. Illegal trade in controlled release opioid tablets is becoming more prevalent. In order to obtain a euphoric effect (high) from such tablets, an abuser may crush the tablet and extract the opioid compound by dissolution for injection, or intranasal administration. Also, the abuser can achieve a euphoric effect from the drug by simply taking the drug orally, after chewing the tablet or grinding it to break the controlled release matrix and converting it to an immediate release product. Therefore, it would be desirable to have a formulation which would prevent the oral abuse of controlled release tablets if crushed to convert it to an immediate release product, without significantly affecting the analgesic action of opioid compounds in the intact controlled release tablet.

WO 01/58447 discloses pharmaceutical combinations of opioid agonists and antagonists in a controlled release matrix. The antagonist is present and released in amounts, over time, that attenuate or reduce the side effects of the opioid agonist, yet in amounts insufficient to block the opioid effect. The preferred antagonist is Naltrexone, which is highly effective when administered orally or parenterally. The antagonist is released only in very small amounts, 100-1000 times less than the opioid. WO '447 is silent with respect to including an anti-abusive amount of antagonist in the dose to prevent abuse. The intravenous use of small amounts of naloxone, 0.25 or 1 µg kg$^{-1}$ hr$^{-1}$, is also disclosed as having attenuating effects.

WO '447 does not present release rates for the antagonist in its CR formulation, but directs those skilled in the art to the Crain patents (U.S. Pat. Nos. 5,767,125; 5,580,876; 5,512,578; and 5,472,943). The Crain patents collectively disclose instant release formulations with "ultra-low" doses of certain antagonists to selectively block only the excitatory opioid receptors to attenuate opioid side effects, without blocking inhibitory receptors, which would lead to opioid blocking. These doses are on the order of pico-molar amounts. Crain '578 suggests that only naltrexone is useful in oral administration and that 1 μg doses are sufficient for attenuating opioid side effects by selectively blocking the excitatory opioid receptors and leaving the inhibitory opioid receptors free for receiving the opioid agonist (which may be administered in lower than normal doses with similar analgesic effect). The normal oral dose of naltrexone is about 50 mg versus "ultra low" does of 1 μg of naltrexone described in Crain '578 patent.

The prior art does not discuss controlled release formulation containing agonist and antagonist to deter abuse. Accordingly, there is a need for a composition that deters abuse in the high opioid-content controlled release formulation prevalent today.

SUMMARY OF THE INVENTION

Abuse-resistant, controlled release opioid tablets are a combination containing an opioid antagonist having a high oral:parenteral potency ratio (i.e. oral:parenteral>1), such as naloxone, at a level insufficient to block the opioid effects or to attenuate the opioid side-effects in the controlled release formulation administered over an extended period, but above that needed to suppress the euphoric effect of the opioid if administered all at once. If the combination tablet is crushed to break the controlled release properties, the opioid and opioid antagonist is released as an immediate release product in a single dose, and the antagonist blocks the euphoric effects of the agonist. The opioid antagonist is contained in a controlled-release matrix and released over time, with the opioid agonist.

DETAILED DESCRIPTION OF THE INVENTION

The present invention employs the principle that certain opioid antagonists are ineffective in low oral doses. Therefore, one can administer a low oral dose over a long period of time (controlled release) from a tablet containing a large, orally effective amount of antagonist, without adversely affecting the action of the opioid. However, if the antagonist is administered all at once, it will block the opioid effect and may induce withdrawal in dependent individuals.

The present invention is intended for use in controlled release compositions. The term, "controlled release" or "CR" when used herein, is intended to refer to tablets intended to release an active pharmaceutical ingredient over an extended period of time, usually over 4 hours, generally 8-12 or up to 24 hours. One method of determining this is to check the intended dosing schedule. Any tablet intended to be taken less frequently than once every four hours should be considered controlled release regardless of labeling as controlled release, sustained release, extended release, etc. Often, these tablets contain polymeric matrices which may be cross-linked. Examples of such controlled release formulations are the Contin® system, produced by Purdue Fredrick Pharmaceuticals, or the TimerX® system by Pennwest Pharmaceuticals. Other controlled release polymers can also be used, such as methacrylate (Eudragit®), hydroxylpropyl methylcellulose (HPMC), or Carbopol®. The present invention may be used with these or other controlled release formulations.

The tablet of the present invention contains an opioid agonist in a controlled release matrix, along with an opioid antagonist. The antagonist is present at such a level, and dispensed at such a rate, that it will not block the action of the opioid agonist when an intact controlled release tablet is taken orally. Crushing the tablet will release sufficient antagonist all at once as an immediate release formulation to block the opioid response and also, induce abstinence. Antagonists need to reach an effective dose to work, so their slow release coupled with fast metabolism means they are maintained at ineffective, low levels in normal, recommended, therapeutic, non-abusive use. This low level of antagonist can be released over a long time period without affecting the therapeutic action of the opioid agonist. Even with sustained release over such long periods, the antagonist does not accumulate to blocking levels, since it is metabolized before it can accumulate to such levels. Because of the nature of the opioid antagonist action, the level of antagonist should be varied with the opioid dosage of the tablet. Also, depending on the antagonist, the oral:parenteral potency ratio, and the release rates, the levels of antagonists employed will vary. Regardless, there should be sufficient antagonist to block the opioid effect (high) and induce withdrawal in dependent individuals, if the tablet is crushed, converting the formulation to immediate release. Under normal conditions, the release rate is not sufficient for blocking the opioid effect nor suitable for selectively blocking the excitatory opioid receptors to attenuate opioid side effects. For Naloxone, the presently preferred antagonist, it is believed that 15 mg (immediate release) should begin to block the opioid receptors and initiate withdrawal.

The specific opioid agonists, antagonists, CR matrices, and the combinations disclosed herein are merely exemplary. Other agonists, antagonists, matrices, and combinations may be used in conjunction with the teachings herein.

The opioid agonist can be any agonist in general use as an analgesic, including, but not limited to, morphine, oxycodone, levorphanol, meperdine, hydrocodone, codeine, dihydrocodeine, hydromorphone, propoxyphene, methadone, and oxymorphone. Specifically, any addictive opioid in a controlled release dosage form is the target of the present invention. Most particularly, controlled release oxycodone has recently been the target of abuse, and would therefore make a good candidate for use in the present invention. Of course, the release rate of the opioid agonist is established to achieve the desired analgesic effect.

Potency of the antagonist is measured as the oral:parenteral potency ratio, which indicates the amount of antagonist required orally to achieve an equivalent effect to an effective parenteral dose. For example, an antagonist having an oral:parenteral potency ratio of 10:1 requires 10 times the parenteral dose to be effective orally. The opioid antagonists used herein will have greater antagonistic effect when administered parenterally than when administered orally (oral:parenteral potency ratio>1). Accordingly, the desired antagonists block the opioid effect and induce withdrawal when administered at relatively low levels parenterally or intranasally. At the same time, these antagonists require relatively large levels to be effective when administered orally for recommended, therapeutic use. Thus, effective parenteral/intranasal doses are ineffective when administered orally. Preferably, the oral:parenteral potency ratio is at least approximately 10:1, more preferably at least approximately 25:1, and most preferably at least approximately 100:1 as is the case with Naloxone. Appropriate opioid antagonists having substantially greater effectiveness when administered by injection than when administered orally, include, but are not limited to: naloxone; naltrexone; N-cyclopropylmethyl-7,8-dihydro-14-hydroxynormorphinone or 21-cyclopropyl z, -(1-hydroxy-1-methylethyl)-6,14-endo-ethano-tetrahydrooripavine (or diphenorphine); and the pharmaceutically-acceptable salts thereof.

It has previously been known that opioid antagonists, such as naloxone, can block opioid receptors and reduce or eliminate the effect of opioids. Such antagonists are useful in treating opioid overdoses and to help treat addiction, in some cases. By blocking opioid receptors, the antagonists reverse and block the response to opioids. The high oral:parenteral potency ratio antagonists, such as naloxone, while very effective when injected, are significantly less effective when taken orally. Therefore, a dosage form designed for oral administration can have a significant amount of opioid antagonist, without adversely affecting the therapeutic efficacy of the opioid. Similarly, these levels of antagonists do not attenuate the side effects of the opioid. Such an antagonist would be effective in deterring intravenous or intranasal abuse when present in low levels, but would be ineffective in deterring oral abuse. Were the tablets to include sufficient antagonist to deter oral abuse, the antagonist would also reduce or inhibit the therapeutic efficacy of the drug. A tablet containing an orally effective amount of antagonists in a CR formulation releasing ineffective amounts of antagonist under normal use would be effective against both oral and parenteral abuse, without minimizing the effectiveness of the opioid under normal use.

The amount of antagonist in the composition will depend on the relative strength of the antagonist, the amount and strength of the opioid, the release rate of the antagonist, and the oral:parenteral potency ratio. In any event, the combination of antagonist type, oral:parenteral potency ratio, quantity, and release rate do not result in blockage of the opioid effect or attenuation of its side effects, when administered orally in its intended, intact dosage form.

Strengths of controlled release opioid tablets vary with the particular opioid used. In the case of oxycodone, strengths of 10, 20, 40, 80, and 160 mg may be used in a controlled release formula. The amount of opioid antagonist (such as naloxone) in such a tablet may also vary from about 2 mg to 40 mg or more. There should be at least 5 to 20 mg (preferably 10 to 20 mg) of naloxone in a tablet to prevent oral abuse by chewing a number of small, low dose tablets or a higher strength tablet. That is, the accumulation of an abusive dose by combining 2 or more low-dose tablets should also accumulate an effective amount of antagonist. Higher dose opioid tablets should contain an effective amount of antagonist without accumulation. Prevention of abuse by parenteral or intranasal administration will also be accomplished, since in the case of injection or snorting, only about 0.2 to 0.4 mg naloxone is needed to antagonize the opioid effect, to induce abstinence in dependent individuals, and to prevent abuse. Therefore the larger amount needed to prevent oral abuse will necessarily prevent abuse by injection or intranasal administration as well.

For oxycodone tablets of 10 or 20 mg tablet strength, the amount of naloxone, opioid antagonist used can range from 5 to 40 mg. As the tablet strength rises, the ratio of opioid to opioid antagonist varies from 1:3 to 4:1, since a 160 mg opioid tablet may contain 80 mg opioid antagonist. Although the ratio can vary, it is preferable to select one ratio for all tablet strengths. Physicians prefer to titrate patients using several low dose tablets which add up to the desired dosage. This is easiest if a constant ratio is maintained. Thus, a constant ratio across tablet strengths is useful even though that ratio can be any appropriate ratio in the range set forth above.

Drug abusers are creative when finding ways to defeat anti-abusive measures. Currently, several methods of oral abuse are contemplated. As discussed above, it should be remembered that the compositions of the invention contain sufficient antagonist to be effective orally and, therefore, necessarily contain a parenterally or intranasally effective blocking amount. Accordingly, parenteral and intranasal abuse are not discussed here.

Abusers may "chew" a single large dose tablet to achieve instant release of an abusive dose of opioid. Compositions containing these abusive amounts of opioid should contain enough antagonist to block oral abuse by "chewing."

Two or more lower dose tablets may be "chewed" together to achieve an abusive dose. To the extent that each tablet itself does not contain an orally, effective amount of antagonist, when combined to an abusive dose, the combined antagonist should be orally effective. That is if, for example, a 10 mg tablet is not sufficient to achieve a high, it need not contain the full orally effective amount of antagonist. If two 10 mg tablets are sufficient for a high, they then should contain a combined amount of antagonist which is effective orally for blocking the opioid effect.

Additionally, two or more high-dose tablets could be taken orally, without crushing, to achieve a "high." Such a combination would take advantage of the CR properties to sustain a high for the entire dosage period up to 12 hours. This type of abuse is uncommon since most abusers want the instant high or rush afforded by the immediate release of the crushed tablets. Such a combination, according to one embodiment of the invention, should also release a blocking amount of antagonist when taken orally without chewing. This arrangement would also prevent the dire effects of accidental overdose. Although this type of arrangement would be beneficial in many situations, it could limit a prescribing doctor's options, and therefore, may not be appropriate in all situations. Tablets according to this embodiment are not preferred, but are certainly within the scope of the invention.

Tablets according to the invention may take into consideration any of the above abusive regimes individually or any combination thereof.

The basic underlying premise of the invention is that the tablet contains 1) an amount of antagonist which is orally effective for blocking the opioid effect and 2) that the antagonist is available, normally, only at levels that are ineffective to block the opioid effect or to attenuate the opioid side-effects. One of the ways to achieve this is to control the release rate of the antagonist. The release rate of the antagonist is best thought of in terms of a percent of the release rate of the opioid agonist. The rate is controlled between approximately 100%-0% of the release rate of the opioid, preferably 100%-25%. Table 1 shows release rates of opioid and antagonist as % released. In the case of 0%, the antagonist is never released unless the tablet is crushed. But, that is the subject of another application.

In the case of Naloxone, the short half-life (about one hour) ensures that the Naloxone does not accumulate to blocking levels, even when released at the same rate as the opioid. In slower release formulations (50% and 75%), the unreleased portion remaining after 10-12 hours passes to the large intestine where the absorption rate is much slower than in the stomach and small intestine. Accordingly, the amount of antagonist released beyond 10-12 hours does not contribute to any blocking or attenuating effect.

These release rates ensure that under normal usage the antagonist has no blocking or attenuating effect. Simultaneously, however, an orally effective blocking dose of the antagonist is present in the event that the CR properties are defeated.

The type and application of CR matrix used will determine release rates. Manipulation of release rates, even of two compounds with two different rates is known in the art. Any known or later developed CR techniques may be used. It is important to remember though, that the antagonist should not be readily distinguishable or separable from the agonist, since would be abusers could possibly use mechanical separation techniques prior to defeating the CR formulation.

TABLE 1

Release Rates from CR formulation

|  | AGONIST | ANTAGONIST (as % of AGONIST release rate) | | |
| --- | --- | --- | --- | --- |
|  |  | 100% | 50% | 25% |
| 1 HR | 20-30% | 20-30% | 10-15% | 5-7.5% |
| 4 HRS | 60-70% | 60-70% | 30-35% | 15-17.5% |
| 10 HRS | >90% | >90% | 45-50% | 22.5-25% |

Release rates are a percentage of agonist or antagonist with respect to its total content in the composition.

The tablets may be made by any traditional method of manufacture of controlled release tablets. Two principal processes are wet process (including wet granulation) and dry process (including direct mixing and roller compaction process.) Exemplary compositions for those processes are reproduced below.

TABLE 2

Preferred Naloxone Ranges for Differing Strengths of Oxycodone Tablets

| Oxycodone (mg) | 10 | 20 | 40 | 80 | 160 |
| --- | --- | --- | --- | --- | --- |
| Naloxone (mg) | 2-10 | 4-20 | 8-40 | 16-80 | 20-160 |

For oxymorphone, the doses for controlled release tablets may be 10, 20, or 40 mg and the naloxone dose ranges may be the same as set forth for oxycodone.

The preferred oxycodone:naloxone ratio is 5:1 to 1:1.

TABLE 3

Formula 1 of Oxycodone HCl 10-mg Tablets with Naloxone

| Component | mg/Tablet | percent (by wt) |
| --- | --- | --- |
| Oxycodone Hydrochloride | 10.00 | 2.22% |
| Naloxone | 10.00 | 2.22% |
| Lactose (spray-dried) | 281.50 | 62.56% |
| Hydroxypropyl Methylcellulose, K100M | 135.00 | 30.00% |
| Silicone Dioxide | 9.00 | 2.00% |
| Magnesium Stearate | 4.50 | 1.00% |
| Total: | 450.00 | 100.00% |

TABLE 4

Formula 2 of Oxycodone HCl 10-mg Tablets with Naloxone

| Component | mg/Tablet | percent (by wt) |
| --- | --- | --- |
| Oxycodone Hydrochloride | 10.00 | 3.77% |
| Naloxone | 10.00 | 3.77% |
| Lactose (spray-dried) | 157.55 | 59.45% |
| Hydroxypropyl Methylcellulose, K100M | 79.50 | 30.00% |
| Silicone Dioxide | 5.30 | 2.00% |
| Magnesium Stearate | 2.65 | 1.00% |
| Total: | 265.00 | 100.00% |

TABLE 5

Formula 3 of Oxycodone HCl 10-mg Tablets with Naloxone

| Component | mg/Tablet | percent (by wt) |
| --- | --- | --- |
| Oxycodone Hydrochloride | 10.00 | 8.33% |
| Naloxone | 10.00 | 8.33% |
| Lactose (spray-dried) | 60.40 | 50.33% |
| Hydroxypropyl Methylcellulose, K100M | 36.00 | 30.00% |
| Silicone Dioxide | 2.40 | 2.00% |
| Magnesium Stearate | 1.20 | 1.00% |
| Total: | 120.00 | 100.00% |

Alternate compositions may also be used. Preferably, tablets according to the present invention will have the following compositions:

| Material | Quantity (%) |
| --- | --- |
| Oxycodone Hydrochloride, USP | 2.000-35.000 |
| Naloxone | 2.000-20.000 |
| Microcrystalline Cellulose, NF (Avicel PH102) | 10.000-50.000 |
| Ammonia Methacrylate Copolymer, NF (Eudragit RSPO) | 30.000-70.000 |
| Colloidal Silicon Dioxide, NF (Cab-O-Sil) | 0-5.000 |
| Sodium Lauryl Sulfate, NF | 0-5.000 |
| Magnesium Hydroxide, USP | 0-2.000 |
| Povidone, USP | 0-15.000 |
| Stearic Acid, NF | 0-5.000 |
| Magnesium Stearate, NF | 0-5.000 |

Dissolution was conducted according to USP XXIV Apparatus 3 (Reciprocating Cylinder) for Formulation 1-3. The apparatus 3 is to simulate the gastrointestinal conditions of human. The 1st hour is at pH 1.2 of 0.1N HC 1. The 2nd and 3rd hours are at pH 4.5 of 10 mM of potassium phosphate monobasic. The conditions after the 3rd hours are at pH 6.8 of 10 mM of potassium phosphate monobasic. All dissolution vessels contain 250 mL of dissolution solution. The dip rate is set at 10 dips per minute. The bath temperature is set at 37.5° C. The HPLC parameters are set as follows: Column—Inertsil ODS 3, 50 mm×4.6 mm, 3 µm particle size. Mobile phase: 80% 30 mM sodium hexanesulfonate pH 3.0+/−1, 20% acetonitrile. Injection volume is 75 µL. Column temperature is 35° C., Flow rate is set at 1.0 mL/min. Wavelength is set at 225 nm. Run time is 5.5 minutes.

Dissolution results for Formulation 1-3 were as follows:

| Formulation 1 | | | | |
| --- | --- | --- | --- | --- |
|  | Tablet not Crushed | | Tablet Crushed | |
| Time | % Oxycodone Dissolved | % Naloxone Dissolved | % Oxycodone Dissolved | % Naloxone Dissolved |
| 0 | 0.0 | 0.0 | 0.0 | 0.0 |
| 1 | 29.8 | 27.8 | 88.2 | 94.6 |
| 2 | 47.8 | 45.4 |  |  |
| 3 | 59.8 | 57.4 |  |  |
| 4 | 68.5 | 65.9 |  |  |
| 8 | 91.1 | 87.5 |  |  |
| 12 | 100.7 | 97.9 |  |  |

| Formulation 2 | | | | |
|---|---|---|---|---|
| | Tablet not Crushed | | Tablet Crushed | |
| Time | % Oxycodone Dissolved | % Naloxone Dissolved | % Oxycodone Dissolved | % Naloxone Dissolved |
| 0 | 0.0 | 0.0 | 0.0 | 0.0 |
| 1 | 40.1 | 37.0 | 104.9 | 102.8 |
| 2 | 63.2 | 60.3 | | |
| 3 | 77.3 | 75.3 | | |
| 4 | 86.5 | 85.2 | | |
| 8 | 105.6 | 106.1 | | |
| 12 | 110.5 | 112.6 | | |

| Formulation 3 | | | | |
|---|---|---|---|---|
| | Tablet not Crushed | | Tablet Crushed | |
| Time | % Oxycodone Dissolved | % Naloxone Dissolved | % Oxycodone Dissolved | % Naloxone Dissolved |
| 0 | 0.0 | 0.0 | 0.0 | 0.0 |
| 1 | 59.0 | 52.5 | 100.5 | 90.9 |
| 2 | 85.4 | 78.0 | | |
| 3 | 97.4 | 90.3 | | |
| 4 | 102.5 | 95.9 | | |
| 8 | 105.4 | 99.7 | | |
| 12 | 105.4 | 99.8 | | |

From these tests, it is evident that under normal, non-crushing use, the amount of antagonist, here naloxone, released over time is insufficient to block the opioid effect. Even Example 3, which has the highest initial release rate of antagonist, only makes about 5 mg naloxone available in the first hour. Due to the short half-life of naloxone, and the slow release rate, the antagonist does not accumulate in the body to a level that blocks the opioid effect. On the other hand, in the crushed tablet, substantially all of the antagonist is available in the first hour. Thus, an opioid blocking amount of antagonist is readily available to deter oral and other forms of abuse. Regardless of the antagonist used, the combination of the antagonist content, the release rate, and the antagonist half-life achieves the goals of the invention to block the opioid effect when administered as for instant release, yet not blocking the opioid effect when administered as intended and recommended as a controlled release formulation.

It is well known that the various opioids have differing relative strengths. Often, these are compared and related to a standard for determining relative doses of each. Although this application discusses opioid content in terms of oxycodone, those skilled in the art will readily appreciate that other opioids, stronger and weaker, can be used in equivalent dosage amounts. Likewise, the antagonist is similarly selected and dosed.

The scope of the invention is not limited to the above examples, which are provided only for purposes of illustration. The above description is written in the context of a tablet. Other oral dosage forms, capable of being made in CR formulations may be used. Among the oral dosage forms available are capsules, caplets, microspheres, gel caps and even liquid formulations.

The invention claimed is:

1. An oral controlled release pharmaceutical composition comprising:
   oxycodone; and
   naloxone;
   wherein the oxycodone and the naloxone are present in a ratio of 5:1 to 1:1; and
   wherein the composition releases the naloxone and the oxycodone such that 45.4-78% of the naloxone is released from the composition over 2 hours.

2. The pharmaceutical composition of claim 1, wherein the oxycodone is present in an amount of 10-160 mg.

3. The pharmaceutical composition of claim 1, wherein the oxycodone is present in an amount of 10-80 mg.

4. The pharmaceutical composition of claim 1, wherein the oxycodone is present in an amount of 10-40 mg.

5. The pharmaceutical composition of claim 1, wherein the oxycodone is present in an amount of 10 mg and the naloxone is present in an amount of 2-10 mg.

6. The pharmaceutical composition of claim 1, wherein the oxycodone is present in an amount of 20 mg and the naloxone is present in an amount of 5-20 mg.

7. The pharmaceutical composition of claim 1, wherein the oxycodone is present in an amount of 40 mg and the naloxone is present in an amount of 8-40 mg.

8. The pharmaceutical composition of claim 1, wherein the oxycodone is present in an amount of 80 mg and the naloxone is present in an amount of 16-80 mg.

9. The pharmaceutical composition of claim 1, wherein the naloxone is present in an amount of 2-160 mg.

10. The pharmaceutical composition of claim 1, wherein the naloxone is present in an amount of 2-40 mg.

11. The pharmaceutical composition of claim 1, wherein the naloxone is present in an amount of 5-20 mg.

12. The pharmaceutical composition of claim 1, wherein the oxycodone and the naloxone are present in a ratio of 4:1 to 1:1.

13. The pharmaceutical composition of claim 1, wherein the oxycodone is in the form of oxycodone hydrochloride.

14. The pharmaceutical composition of claim 1, wherein the naloxone is in the form of a pharmaceutically acceptable salt thereof.

15. The pharmaceutical composition of claim 1, wherein the release rate of the naloxone is approximately 100 percent to approximately 25 percent of the release rate of the oxycodone.

16. The pharmaceutical composition of claim 1, wherein the release rate of the naloxone is approximately 100 percent of the release rate of the oxycodone.

17. The pharmaceutical composition of claim 1, wherein >90% of the oxycodone is released from the composition over 10 hours.

18. The pharmaceutical composition of claim 1, wherein >90% of the naloxone is released from the composition over 10 hours.

19. The pharmaceutical composition of claim 1, wherein the oxycodone and the naloxone are released over a period greater than 4 hours.

20. The pharmaceutical composition of claim 1, wherein the composition further comprises a controlled release matrix that contains the oxycodone and the naloxone.

21. The pharmaceutical composition of claim 1, wherein the pharmaceutical composition is in the form of a tablet.

22. The pharmaceutical composition of claim 1, wherein the naloxone is not readily separable from the oxycodone.

23. The pharmaceutical composition of claim 1, wherein sufficient naloxone is released to block the opioid euphoric effect when the pharmaceutical composition is crushed.

24. The pharmaceutical composition of claim 1, wherein the naloxone is released as immediate release capable of inducing withdrawal in dependent individuals if the pharmaceutical composition is crushed and the controlled release properties broken.

25. The pharmaceutical composition of claim 1, wherein the naloxone is released at a rate ineffective for inducing withdrawal when the pharmaceutical composition is taken orally in intact form.

26. The pharmaceutical composition of claim 1, wherein the release of the naloxone does not block the action of the oxycodone when the controlled release properties are intact.

27. A method of treating pain comprising administering to a patient in need thereof the pharmaceutical composition of claim 1.

28. An oral controlled release pharmaceutical composition comprising:
   oxycodone hydrochloride; and
   2-40 mg of a pharmaceutically acceptable salt of naloxone;
   wherein the oxycodone hydrochloride and the pharmaceutically acceptable salt of naloxone are present in a ratio of 4:1 to 1:1;
   wherein the composition releases the pharmaceutically acceptable salt of naloxone and the oxycodone hydrochloride such that 45.4-78% of the pharmaceutically acceptable salt of naloxone is released from the composition over 2 hours.

29. The pharmaceutical composition of claim 28, wherein the oxycodone is present in an amount of 10, 20, 40, or 80 mg.

30. The pharmaceutical composition of claim 28, wherein the release rate of the naloxone is approximately 100 percent of the release rate of the oxycodone.

* * * * *